(12) United States Patent
Santra et al.

(10) Patent No.: US 8,791,285 B2
(45) Date of Patent: Jul. 29, 2014

(54) ACTIVATABLE NANOPROBES FOR INTRACELLULAR DRUG DELIVERY

(75) Inventors: Swadeshmukul Santra, Orlando, FL (US); James Turkson, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 210 days.

(21) Appl. No.: 13/493,815

(22) Filed: Jun. 11, 2012

(65) Prior Publication Data

US 2013/0006007 A1 Jan. 3, 2013

Related U.S. Application Data

(60) Provisional application No. 61/495,992, filed on Jun. 11, 2011.

(51) Int. Cl.
*C07F 19/00* (2006.01)
*A61K 38/00* (2006.01)
*G01N 33/574* (2006.01)
*A61B 8/00* (2006.01)

(52) U.S. Cl.
USPC .............. 556/31; 424/9.6; 424/490; 424/497; 435/7.23; 514/19.2; 977/709; 977/710

(58) Field of Classification Search
USPC .......... 424/9.6, 490, 497; 435/7.23; 514/19.2; 556/31; 977/709, 710
See application file for complete search history.

(56) References Cited

U.S. PATENT DOCUMENTS

| | | | |
|---|---|---|---|
| 2006/0228554 A1 | 10/2006 | Tan et al. | |
| 2007/0190160 A1* | 8/2007 | Turos et al. | 424/490 |
| 2007/0264719 A1 | 11/2007 | Santra et al. | |
| 2007/0269382 A1 | 11/2007 | Santra et al. | |
| 2007/0298006 A1* | 12/2007 | Tomalia et al. | 424/78.03 |
| 2010/0183504 A1* | 7/2010 | Chen | 424/1.29 |
| 2010/0254911 A1 | 10/2010 | Sharma et al. | |
| 2011/0014296 A1* | 1/2011 | Chen et al. | 424/490 |
| 2011/0021745 A1 | 1/2011 | Santra et al. | |

OTHER PUBLICATIONS

Ferrari, M., "Cancer nanotechnology: Opportunities and challenges", Nature Reviews Cancer 5, pp. 161-171 (2005).
Peer, D., et al., "Nanocarriers as an emerging platform for cancer therapy", Nature Nanotechnology 2, pp. 751-760 (2007).
Foy, S.P., et al., "Optical Imaging and Magnetic Field Targeting of Magnetic Nanoparticles in Tumors", ACS Nano 4, pp. 5217-5224 (2010).
John, R., et al., "In vivo magnetomotive optical molecular imaging using targeted magnetic nanoprobes", Proceedings of the National Academy of Sciences of the United States of America 107, pp. 8085-8090 (2010).
Lee, J.H., et al., "All-in-One Target-Cell-Specific Magnetic Nanoparticles for Simultaneous Molecular Imaging and siRNA Delivery", Angewandte Chemie-International Edition 48, pp. 4174-4179 (2009).

(Continued)

*Primary Examiner* — Porfirio Nazario Gonzalez
(74) *Attorney, Agent, or Firm* — Timothy H. Van Dyke; Beusse, Wolter, Sanks & Maire, P.A.

(57) ABSTRACT

An activatable nanoprobe is provided having a core component and an active agent associated with the core component via a bond configured to be cleaved upon exposure to an endogenous compound.

20 Claims, 20 Drawing Sheets
(19 of 20 Drawing Sheet(s) Filed in Color)

(56) References Cited

OTHER PUBLICATIONS

Mulder, W.J.M., et al., "Nanoparticulate Assemblies of Amphiphiles and Diagnostically Active Materials for Multimodality Imaging", Accounts of Chemical Research 42, pp. 904-914 (2009).
Park, K., et al., "New Generation of Multifunctional Nanoparticles for Cancer Imaging and Therapy", Advanced Functional Materials 19, pp. 1553-1566 (2009).
Kircher, M.F. et al., "A multimodal nanoparticle for preoperative magnetic resonance imaging and intraoperative optical brain tumor delineation", Cancer Research 63, pp. 8122-8125 (2003).
McCann, C.M., et al., "Combined magnetic resonance and fluorescence imaging of the living mouse brain reveals glioma response to chemotherapy", Neuroimage 45, pp. 360-369 (2009).
Erogbogbo, F., et al., "Biocompatible Magnetofluorescent Probes: Luminescent Silicon Quantum Dots Coupled with Superparamagnetic Iron(III) Oxide", ACS Nano 4, pp. 5131-5138 (2010).
Mulder, W.J.M., et al., "Molecular imaging of tumor angiogenesis using alpha v beta 3-integrin targeted multimodal quantum dots", Angiogenesis 12, pp. 17-24 (2009).
Mulder, W.J.M., et al., "Quantum dots for multimodal molecular imaging of angiogenesis", Angiogenesis 13, pp. 131-134 (2010).
Trehin, R., et al., "Fluorescent nanoparticle uptake for brain tumor visualization", Neoplasia 8, pp. 302-311 (2006).
Zrazhevskiy, P., et al., "Designing multifunctional quantum dots for bioimaging, detection, and drug delivery", Chemical Society Reviews 39, pp. 4326-4354 (2010).
Cheng, S.H., et al. "Tri-functionalization of mesoporous silica nanoparticles for comprehensive cancer theranostics—the trio of imaging, targeting and therapy", Journal of Materials Chemistry 20, pp. 6149-6157 (2010).
Medintz, I.L., et al., "Quantum-dot/dopamine bioconjugates function as redox coupled assemblies for in vitro and intracellular pH sensing", Nature Materials 9, pp. 676-684 (2010).
Medintz, I.L., et al., "Proteolytic activity monitored by fluorescence resonance energy transfer through quantum-dot-peptide conjugates", Nature Materials 5, pp. 581-589 (2006).
Medintz, I.L., et al., "Quantum dot bioconjugates for imaging, labelling and sensing", Nature Materials 4, pp. 435-446 (2005).
Medintz, I.L., et al., "Self-assembled nanoscale biosensors based on quantum dot FRET donors", Nature Materials 2, pp. 630-638 (2003).
Banerjee, S., et al, "Quantum Dot-Based Off/On Probe for Detection of Glutathione", Journal of Physical Chemistry C 113, pp. 9659-9663 (2009).
Banerjee, S., et al., "A simple strategy for quantum dot assisted selective detection of cadmium ions", Chemical Communications, pp. 3037-3039 (2008).
Bagalkot, V., et al. "Quantum dot—Aptamer conjugates for synchronous cancer imaging, therapy, and sensing of drug delivery based on Bi-fluorescence resonance energy transfer", Nano Letters 7, pp. 3065-3070 (2007).
Gao, J.H., et al., "Multifunctional Magnetic Nanoparticles: Design, Synthesis, and Biomedical Applications", Accounts of Chemical Research 42, pp. 1097-1107 (2009).
Liong, M., et al., "Multifunctional inorganic nanoparticles for imaging, targeting, and drug delivery", Acs Nano 2, pp. 889-896 (2008).
Mulder, W.J.M., et al. "Magnetic and fluorescent nanoparticles for multimodality imaging", Nanomedicine 2, pp. 307-324 (2007).
Tietze, F., "Enzymic method for quantitative determination of nanogram amounts of total and oxidized glutathione—applications to mammalian blood and other tissues", Analytical Biochemistry 27, 502- (1969).
Coles, B. et al, "The role of glutathione and glutathione transferases in chemical carcinogenesis", Critical Reviews in Biochemistry and Molecular Biology 25, pp. 47-70 (1990).
Pompella, A., et al, "The changing faces of glutathione, a cellular protagonist", Biochemical Pharmacology 66, pp. 1499-1503 (2003).
Meier, R., et al. "Breast Cancers: MR Imaging of Folate-Receptor Expression with the Folate-Specific Nanoparticle P1133", Radiology 255, pp. 527-535 (2010).
Zhang, X.L., et al. "A novel small-molecule disrupts Stat3 SH2 domain-phosphotyrosine interactions and Stat3-dependent tumor processes", Biochemical Pharmacology 79, pp. 1398-1409 (2010).
Fletcher, S., et al. "Disruption of Transcriptionally Active Stat3 Dimers with Non-phosphorylated, Salicylic Acid-Based Small Molecules: Potent in vitro and Tumor Cell Activities", Chembiochem 10, pp. 1959-1964 (2009).
Siddiquee, K., et al., "Selective chemical probe inhibitor of Stat3, identified through structure-based virtual screening, induces antitumor activity", Proceedings of the National Academy of Sciences of the United States of America 104, pp. 7391-7396 (2007).
Jones, G., et al., "Development and validation of a genetic algorithm for flexible docking", Journal of Molecular Biology 267, pp. 727-748 (1997).
Santra, S., et al., "Synthesis of water-dispersible fluorescent, radio-opaque, and paramagnetic CdS : Mn/ZnS quantum dots: A multifunctional probe for bioimaging", Journal of the American Chemical Society 127, pp. 1656-1657 (2005).
Michalet, X. et al., "Quantum Dots for Live Cells, in Vivo Imaging, and Diagnostics", Science 307, pp. 538-544, doi:10.1126/science.1104274 (2005).
Samia, A. C. S.,et al., "Semiconductor Quantum Dots for Photodynamic Therapy", Journal of the American Chemical Society 125, pp. 15736-15737, doi:10.1021/ja0386905 (2003).
Shi, L., et al., "Synthesis and Application of Quantum Dots FRET-Based Protease Sensors", Journal of the American Chemical Society 128, pp. 10378-10379, doi:10.1021/ja063509o (2006).
Zhang, C.et al., "Single Quantum-Dot-Based Aptameric Nanosensor for Cocaine", Analytical Chemistry 81, pp. 3051-3055, doi:10.1021/ac802737b (2009).
Banerjee, S. et al., "Semiconductor CdS:Mn/ZnS quantum dots for sensing applications" vol. 7674 (SPIE, 2010).
Mitra, R. N. et al. "An activatable multimodal/multifunctional nanoprobe for direct imaging of intracellular drug delivery", Biomaterials 33, pp. 1500-1508, doi:10.1016/j.biomaterials.2011.10.068 (2012).

* cited by examiner

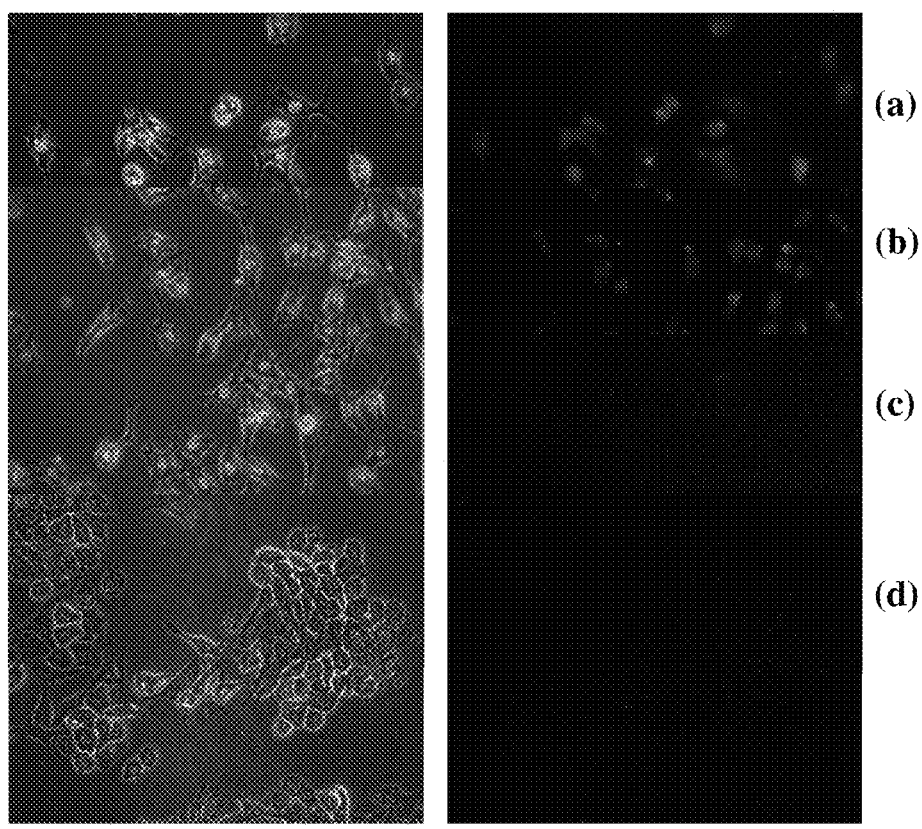
FIG. 3a-d

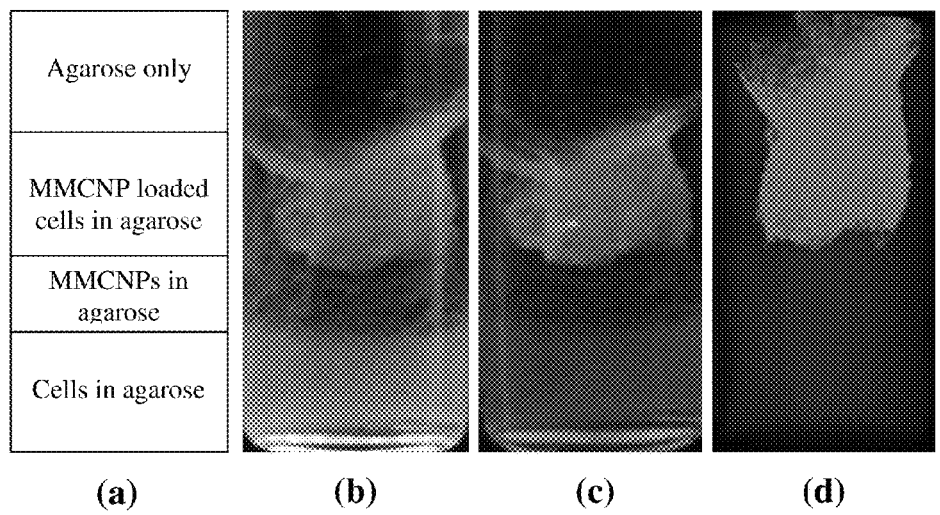
FIGS. 5a-d
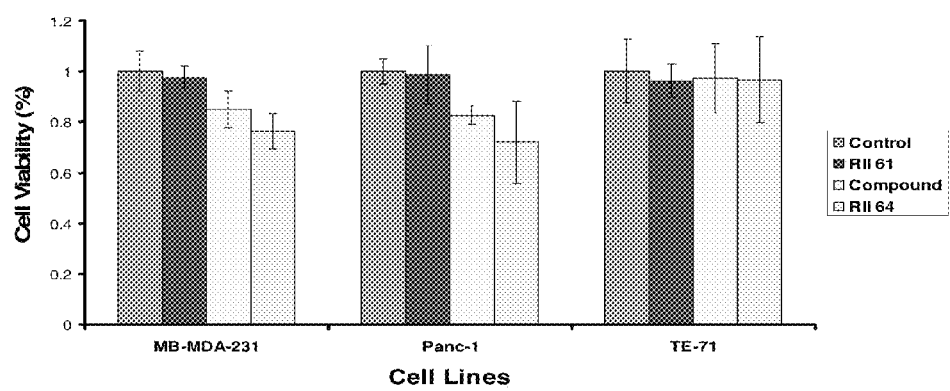
FIG. 6

BP-1-102

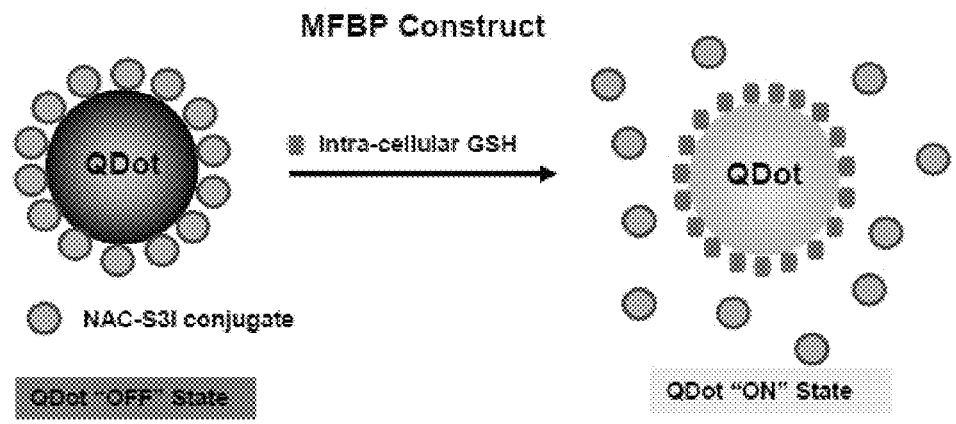
FIG. 17
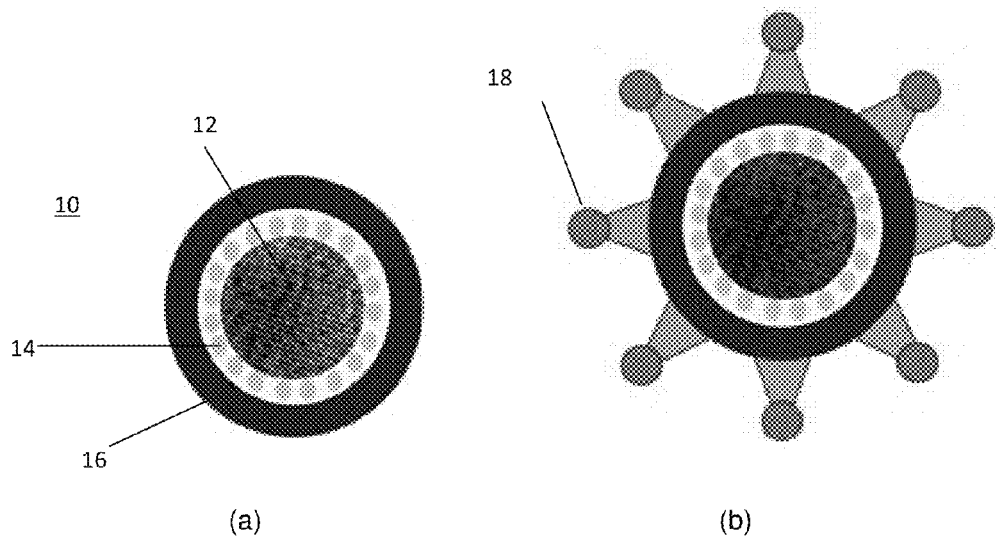
FIGS. 18a-b

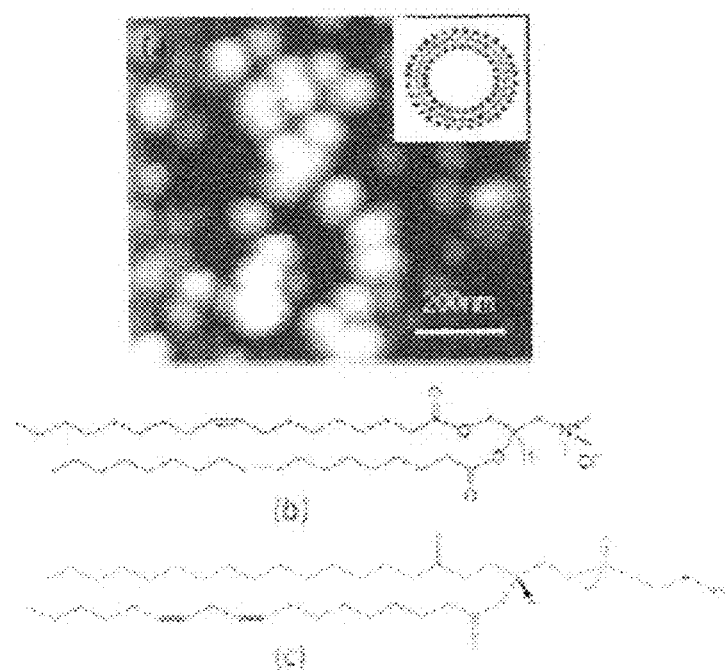
FIGS. 19a-c

1. GSH coated QD
2. GSH coated QD +2.6 mg/L EDTA
3. GSH coated QD +6 mg/L EDTA
4. GSH coated QD +7.6 mg/L EDTA
5. GSH coated QD +10 mg/L EDTA
6. GSH coated QD+12.6mg/L EDTA

ACTIVATABLE NANOPROBES FOR INTRACELLULAR DRUG DELIVERY

CROSS-REFERENCE TO RELATED APPLICATIONS

This application is related to U.S. Provisional Application No. 61,495,992 filed Jun. 11, 2011. Priority to this application is claimed under 35 USC §119, and is incorporated herein.

STATEMENT OF GOVERNMENT RIGHTS

The work leading to this invention was partly supported by grants from the NIH Grant No. 2P01HL059412-11A1 and NSF Grant No. 0506560. Accordingly, the government may have certain rights in the invention, as specified by law.

FIELD OF THE INVENTION

The present invention relates to the field of activatable nanoprobes, and in certain embodiments, to multifunctional activatable nanoprobes.

BACKGROUND OF THE INVENTION

Cancer nanotechnology is a rapidly growing research area in nanomedicine involving disease diagnostics and therapy[1,2]. During the past decade, engineered nanoparticles integrated with multimodality/multifunctionality have enabled imaging of cancer cells with high sensitivity and demonstrated successful delivery of pre-loaded therapeutic drugs in a targeted manner[3-7]. Multimodal nanoparticles that are integrated with optical and magnetic imaging modalities[8,9] have demonstrated strong potential to facilitate pre-operative cancer diagnosis by MRI and optical based imaging[10-13], to provide intra-operative surgical guidance (by optically demarcating tumor tissue from healthy tissue), and to track tumor metastasis[2,7,8].

Current nanoparticle technology allows for imaging of particles carrying therapeutic drugs[3,6,7,10,14,15]. However, no activatable drug delivery system has been reported to date that has demonstrated the ability to directly confirm intracellular drug release upon reaction with a cytosolic biomolecule. Up until now, challenges in designing and constructing a nanoparticle integrating imaging, monitoring, and therapeutic functionalities in a single unit have restricted the fabrication of such a nanoparticle system.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3a-3d includes phase-contrast (left panel) and corresponding epi-fluorescence (right panel) microscopy images of: (a) MDA-MB-231 cells incubated with MMCNPs for 3 hours, showing significant Qdot fluorescence. This confirms extensive folate receptor mediated uptake of the MMCNPs; (b) MDA-MB-231 cells incubated with MMCNPs for 24 hours, again showing significant Qdot fluorescence that is similar to the 3 hour incubation experiment. These data show that uptake of MMCNPs and subsequent restoration of Qdot fluorescence (indicative of STAT-3 release) occurs in less than 3 hours; (c) control experiment performed with MDA-MB-231 cells to which no MMCNPs were added. As expected only a minor cellular autofluorescence is observed; (d) control experiment performed with mouse thymus stromal epithelial cells, TE-71 incubated with MMCNPs for 24 hours. Similar to the control experiment shown in panel (c) only background autofluorescence is observed at locations that correspond to the locations of the cells, with no evidence of uptake of MMCNPs by the TE-71 normal cells. This control experiment validates that the delivery of MMCNPs is highly targeted to MDA-MB-231 cells, which over-express folate receptors.

FIGS. 5a-d show: (a) a schematic of agar phantom design. The agar phantom consists of four layers. From bottom to top these layers are: MDA-MB-231 cells embedded in agar (control), MMCNPs embedded in agar (control), MDA-MB-231 cells loaded with the MMCNPs embedded in agar (sample) and agar layer, respectively. (b) a digital photograph of agar phantom; and (c) a corresponding digital photograph of agar phantom under 366 nm multiband UV irradiation. The MDA-MB-231 cells loaded with the MMCNPs emit red fluorescence that is clearly visible to the naked eye. Control cells do not show any detectable fluorescence emission. (d) an MRI image of agar phantom. The MDA-MB-231 cells loaded with the MMCNPs show strong MRI signal (indicated with false red color) in contrast with the control cells.

FIG. 6 shows results from a CyQuant® cell viability assay performed on human breast (MB-MDA-231) and pancreatic (Panc-1) cancer lines, and mouse thymus stromal epithelial line, TE-71. Cells were untreated (Control) or treated for 24 hours with MMCNPs to which no STAT-3 inhibitor was attached (RII 61), STAT-3 inhibitor only (Compound), and MMCNPs (RII 64). Compared to untreated (Control), the viability of cells treated with MMCNPs to which no STAT-3 is attached (RII 61) was attached is not significantly different, indicating that the MMCNP itself do not compromise cell viability. By contrast, the cells treated with 50 μM STAT-3 inhibitor only (Compound) showed about a 15-20% decrease in cell viability, while cells treated with fully functional MMCNPs to which STAT-3 inhibitor was attached showed nearly 30% decrease in cell viability, even though the amount of STAT-3 inhibitor contained in the about 5 μg of MMCNP administered in about 100 μL of cell media was expected to be less than the about 50 μM that was directly added to the cells in the other study. This key observation demonstrates the effectiveness of the reported nanoparticle design in highly targeted drug delivery to the cancer cells while maximizing cancer cell death with reduced amounts of drugs used compared to conventional approaches. Even though the MMCNP's consume much less STAT3 drug, the delivery efficiency is dramatically increased, thus resulting in increased therapeutic efficiency while minimizing the potential for medical side effects due to the presence of excess free drug.

FIG. 17 is a schematic illustrating sensing of cargo release by a Qdot core due to intracellular GSH.

FIGS. 18a-b shows a nanoparticle having a CdS:Mn/ZnS quantum dot core, to which an S3I inhibitor drug will be covalently linked via a cleavable disulfide bond linkage. (a) a lipid bilayer may be overcoated on the surface of the S3I conjugated CdS:Mn/ZnS quantum dots. (b) the lipid bilayer may be further functionalized with folic acid to target cancer cells that overexpress folate receptors, or with TAT peptide (a cell-penetrating peptide).

FIGS. 19a-c show (a) an AFM image of zwitterionic (DC8, 9PC) lipid vesicles and chemical structures of (b) DOTAP and (c) PtdEtn.

DETAILED DESCRIPTION OF THE INVENTION

Figure 1A:
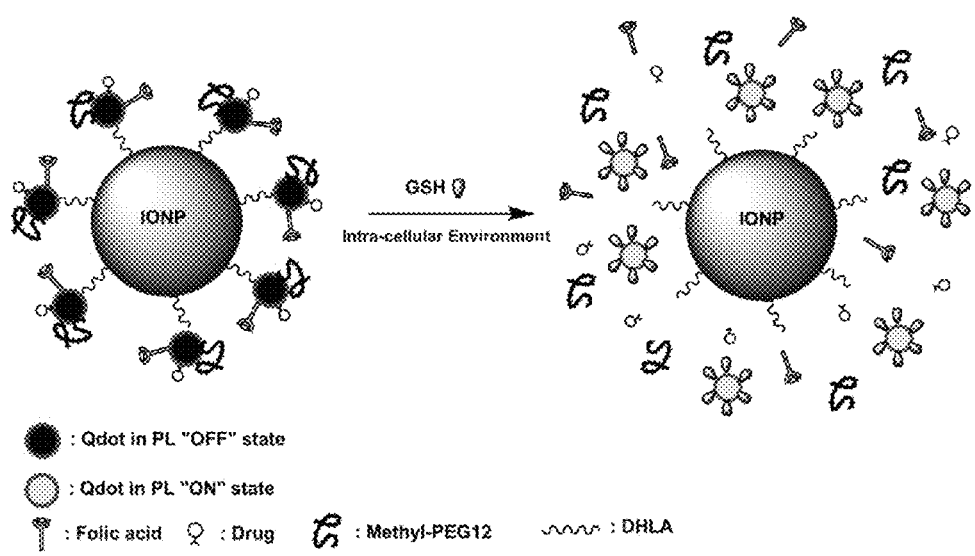
FIG. 1a shows an optically activatable nanoprobe in an "off" state and an "on" state in accordance with an aspect of the present invention.

The present inventors have developed new and unique activatable nanoprobes that may deliver active agents, and in some embodiments, may also be optically and magnetically imageable, targetable, and/or capable of reporting on intracellular drug release events. In one particular exemplary embodiment, an optically activatable nanoprobe is provided that comprises an inorganic core, e.g., a super-paramagnetic iron oxide nanoparticle core (IONP), associated with satellite quantum dots (Qdots), e.g., CdS:Mn/ZnS quantum dots, where the Qdots themselves are further functionalized with an active agent, a targerting agent, and a hydrophilic dispersing agent. Advantageously, the Qdot luminescence is quenched in this nanoprobe ("OFF" state) due to combined electron/energy transfer mediated quenching processes involving IONP, targeting agent and active agents. Upon intracellular uptake, the nanoprobe is exposed to a cytosolic glutathione (GSH)-containing environment resulting in restoration of the Qdot luminescence ("ON" state), which reports on uptake and drug release. Probe functionality was validated using fluorescence and MR measurements, as well as in vitro studies using cancer cells that overexpress folate receptors.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refers to—values that are ±10% of the stated value.

As used herein, the term "active agent" includes any synthetic or natural element or compound, which when introduced into a mammal causes a desired response, such as an optical or biological response.

As used herein, the term "activatable" refers to an agent capable of being released from an associated substrate, e.g., core, upon exposure to a predetermined compound. For example and without limitation, an activatable active agent may include an active agent that is released from a core component upon exposure to an endogenous molecule, such as glutathione, that cleaves a bond between the active agent and the core component.

As used herein, the term "aptamer" refers to any oligonucleic acid or peptide molecules that bind to a specific target molecule.

As used herein, the terms "chitosan" or "chitosan polymer" refer to chitosan (also known as poliglusam, deacetylchitin, poly-(D)glucosamine) and any derivatives thereof. The chitosan polymer is typically composed of a linear polysaccharide of randomly distributed β-(1-4)-linked D-glucosamine (deacetylated unit) and/or N-acetyl-D-glucosamine (acetylated unit) units. The general terms "chitosan" or "chitosan polymer" as used herein may also refer to chitosan or chitosan having one or more molecules attached thereto, e.g., bonded, or conjugated, thereto, such as an imaging agent, a target-specific ligand, or a biologically active compound. Exemplary derivatives of chitosan include trimethylchitosan (where the amino group has been trimethylated) or quaternized chitosan. Advantageously, chitosan has a plurality of amine functional groups, which as set forth below, may be utilized for the attachment of various agents thereto, such as imaging agents, target-specific ligands, and/or biologically active agents.

As used herein, "folate species" or "folate" refers to folate, folic acid, derivatives thereof, or analogs thereof.

As used herein, the terms "bonded," "linked," "labeled," "attached," "conjugated," and variations thereof are intended to be used interchangeably and may refer to covalent, ionic, Van der Waals, or hydrogen bonding, for example.

As used herein, the term "hydrophilic" refers to any substance having an affinity for water and tending to dissolve in, mix with, or swell in a water or aqueous medium.

As used herein, the term "hydrophobic" refers to any substance not having an affinity for water and tending not to dissolve in, mix with, or swell in a water or aqueous medium.

As used herein, the term "surfactant" refers to a wetting agent that lowers the surface tension of a liquid, thereby allowing easier spreading and the lowering of the interfacial tension between two liquids.

As used herein, the term "STAT" refers to signal transducers and activators of transcription, which represent a family of proteins that, when activated by protein tyrosine kinases in the cytoplasm of the cell, migrate to the nucleus and activate gene transcription.

In accordance with one aspect of the present invention, there is provided an activatable nanoprobe comprising a core component and an active agent associated with the core component via a bond configured to be cleaved upon exposure to an endogenous compound.

In accordance with one aspect, there is provided an activatable nanoprobe comprising a core component and an activatable active agent associated with the core component. A lipid vesicle at least partially or fully encases the activatable agent and the core component.

In accordance with another aspect, there is an optically activatable nanoprobe comprising an inorganic core and a Qdot linked to the inorganic core. At least one ligand is linked to the Qdot. The one or more ligands, which are typically electron-rich, are effective to reduce luminescence of the quantum dot when linked thereto. In this way, the Qdot luminescence is quenched in this nanocomposite probe ("off state") due to electron/energy transfer quenching processes between the inorganic core and the at least one ligand. In one embodiment, the at least one ligand comprises at least one of a biologically active agent, a targeting agent, a hydrophilic dispersing agent, or combinations thereof.

In accordance with another aspect, there is provided an optically activatable nanoprobe for monitoring intracellular drug delivery. The nanoprobe comprises a core component; and at least one ligand linked to the core component. The at least one ligand comprises at least one of an active agent, a targeting agent, an imaging agent, a hydrophilic dispersing agent, and combinations thereof. The at least one ligand is effective to reduce luminescence of the quantum dot when linked thereto.

In accordance with another aspect, there is provided an optically activatable nanoprobe for monitoring intracellular drug delivery. The optically activatable nanoprobe comprises an inorganic core and a plurality of quantum dots linked to the inorganic core. A plurality of ligands are linked to respective ones of the plurality of quantum dots. The plurality of ligands include each of a biologically active agent, a targeting agent, and a hydrophilic dispersing agent. Since the ligands are electron rich, the ligands collectively reduce luminescence of the of the quantum dot when linked thereto.

In accordance with another aspect, there is provided an optically activatable nanoprobe comprising a quantum dot core and at least one ligand linked to the quantum dot core. A chitosan-based shell surrounds the quantum dot core and the at least one ligand.

In accordance with another aspect, there is provided a method for monitoring intracellular drug delivery within a subject. The method comprises administering to the subject an effective amount of an optically activatable nanoprobe. The optically activatable nanoprobe comprises an inorganic core, a plurality of quantum dots linked to the inorganic core, and at least an active agent linked to the respective ones of the quantum dots. Upon intracellular uptake of the nanoprobe, a linkage between the active agents and the quantum dots is cleaved to allow the plurality of quantum dots to transfer from a quenched state, wherein the luminescence of the plurality of quantum dots is quenched, to a luminescent state, wherein the luminescence of the plurality of quantum dot is activated. In one embodiment, the method further comprises detecting a presence of the plurality of quantum dots, wherein an increase in luminescence of the plurality of quantum dots is indicative of a release of the active agent intracellularly. In one embodiment, the at least one ligand comprises each of an active agent, a targeting agent, an imaging agent, and a hydrophilic dispersing agent, or a combination thereof.

In yet another aspect, there is provided a method for monitoring intracellular drug delivery within a subject. The method comprises administering to the subject an effective amount of an optically activatable nanoprobe. The optically activatable nanoprobe comprises a core component comprising a quantum dot and an active agent linked to the quantum dot. Upon intracellular uptake of the nanoprobe, a linkage between the active agent and the core component is cleaved to allow for release of the active agent and to allow the quantum dot to transfer from a quenched state, wherein the luminescence of the plurality of quantum dot is quenched, to a luminescent state, wherein the luminescence of the plurality of quantum dots is activated. The method further comprises detecting a presence of the quantum dot, wherein an increase in luminescence of the quantum dot is indicative of a release of the active agent intracellularly.

In yet another aspect, there is provided an activatable nanoprobe comprising a core component; an activatable active agent associated with the core component; and a lipid vesicle at least partially or fully encasing the activatable agent and the core component.

In still another aspect, there is provided an optically activatable nanoprobe comprising: an inorganic core; a plurality of quantum dots about the inorganic core and linked to the inorganic core; and a hydrophilic dispersing agent linked to respective ones of a plurality of the quantum dots.

In still another aspect, there is provided a method for making optically activatable nanoprobes. The method comprises obtaining a plurality of nanoparticles comprising an inorganic core and obtaining a plurality of quantum dots. Further, the method comprises linking the plurality of quantum dots to the inorganic core; and linking an active agent, a targeting agent, and a hydrophilic dispersing agent to respective ones of the plurality of quantum dots.

In yet another aspect, there is provided a method for monitoring intracellular drug delivery within a subject in whom an effective amount of an optically activatable nanoprobe has been administered. The optically activatable nanoprobe comprises an inorganic core; a plurality of quantum dots linked to the inorganic core, and at least one ligand linked to respective ones of the plurality of quantum dots, the at least one ligand comprising at least an active agent linked to the quantum dot by a linkage; and wherein, upon intracellular uptake of the nanoprobe, a linkage between the active agent and a respective quantum dot is cleaved to allow for release of the active agent and to allow the plurality of quantum dots to transfer from a quenched state, wherein the luminescence of the plurality of quantum dots is quenched, to a luminescent state, and wherein the luminescence of the plurality of quantum dot is activated. The method further comprises confirming release of the biologically active agent by detecting a presence of the plurality of quantum dots in the luminescent state.

In yet another aspect, there is provided an optically activatable nanoprobe comprising a core component comprising a quantum dot; and a coating comprising a hydrophilic dispersing agent at least partially surrounding the core component.

In certain aspects, the nanoprobes include a core component. In one embodiment, the core component comprises an inorganic core, which allows for the attachment of a plurality of a Qdots to be disposed about the inorganic core. In this way, a single activatable nanoprobe may have a plurality of quantum dots attached thereto for signal enhancement in monitoring applications. In one embodiment, the inorganic core comprises a paramagnetic material. In a particular embodiment, the inorganic core comprises iron oxide. A super-paramagnetic iron oxide nanoparticle is an excellent MRI contrast agent (also called a T2 contrast agent). Utilizing iron oxide in the inorganic core facilitates imaging of MMCNPs by MRI. It also assists in purification, as an external permanent magnet can be implemented to separate MMCNPs magnetically from the reaction mixture.

The Qdots may comprise a semiconductor crystal whose size is on the order of just a few nanometers and that exhibits quantum confinement. Typically, Qdots contain anywhere from about 100 to about 1,000 essentially free electrons and range from about 2 nm to about 10 nm in size, or about 10 to about 50 atoms, in diameter. One of the optical features of an excitonic Qdot noticeable to the unaided eye is coloration. While the material which makes up a quantum dot is significant, more significant in terms of coloration is the size. The larger the Qdot, the redder (the more towards the longer wavelength end of the electromagnetic spectrum) they fluoresce. The smaller the Qdot, the bluer (the more towards the short wavelength end) it is. The coloration is directly related to the energy levels of the Qdot. Quantitatively speaking, the band gap energy that determines the energy (and hence color) of the fluoresced light is approximately inversely proportional to the square of the size of the Qdot. Larger Qdots have more energy levels, which are more closely spaced. This allows the Qdot to absorb photons containing less energy, e.g., those closer to the red end of the spectrum.

In certain embodiments, the Qdots include a semiconductor nanocrystal core and a wide band-gap semiconductor nanocrystalline shell (coating) disposed on the surface of the nanocrystal core, which is typically different from the material used for the nanocrystal core. The semiconductor coating may define a fully or partially passivating semiconductor coating layer. Exemplary materials for the nanocrystal core and the semiconducting coating of the quantum dot include, but are not limited to, zinc sulfide, zinc selenide, zinc telluride, cadmium sulfide, cadmium selenide, cadmium telluride, mercury sulfide, mercury selenide, mercury telluride, magnesium telluride, aluminum phosphide, aluminum arsenide, aluminum antimonide, gallium nitride, gallium phosphide, gallium arsenide, gallium antimonide, indium nitride, indium phosphide, indium arsenide, indium antimonide, aluminum sulfide, lead sulfide, lead selenide, germanium, silicon, other group II-group VI compounds, group III-group V compounds, group IV compounds, and alloys, compounds, or mixtures thereof. In one embodiment, the semiconductor coating has a band gap greater than the band gap of the nanocrystal core. In some embodiments, the core material can also be doped with one or more suitable dopants, such as manganese (Mn) or copper (Cu). In the examples below, a nanoprobe comprising an iron oxide nanoparticle core associated with satellite CdS:Mn/ZnS Qdots was formed, although it is understood the present invention is not so limited. In another embodiment, the Qdots may comprise ZnS:Mn/ZnS Qdots (non-heavy metal containing Qdots such as cadmium or arsenic).

In particular embodiments, a coupling agent may be provided to link the Qdots to the inorganic core. In one embodiment, the coupling agent comprises a heterobifunctional cross-linking compound that can link to the inorganic core at one location thereon and can link to a respective Qdot at a location thereon. In one embodiment, the coupling agent comprises dihydrolipoic acid (DHLA), which can link the inorganic core thereto through its carboxyl end and link to a respective Qdot via its bidentate thiol bonds.

Either or both of the inorganic core or the quantum dots can be modified with the coupling agent prior to addition of the other of the components. In one embodiment, the coupling agent is provided as a coating over the inorganic core. As set forth below, in one embodiment, to minimize the possibility of cross-linking when using a coupling agent, e.g., DHLA, the addition of the modified inorganic core particles to unmodified quantum dots may be done slowly and in a controlled manner.

When the ligand comprises a targeting agent, the targeting agent may be any compound having an affinity for a predetermined molecular target. In one embodiment, the targeting agent comprises a folate species, which may be folate, folic acid, or derivatives thereof. Examples of folate derivatives include, but are not limited to, dihydrofolate, tetrahydrofolate, 5-methyl-tetrahydrofolate and 5,10-methylene tetrahydrofolate. Humans and other mammals express a number of proteins that bind to folate and transport it into cells. For example, in humans, alpha and beta folate receptors have been identified, each of which can occur in several isoforms (e.g. as a result of differential glycosylation). These proteins are referred to as "folate receptors." Thus, a folate receptor is considered to be any protein expressed on the surface of a cell, such as a cancer cell, which binds folate in preference to other moieties or compounds. In one embodiment, the targeting agent is selected to specifically target these folate receptors in a mammalian subject.

Additionally, in other embodiments, the targeting agent may be one or more of an aptamer, a peptide, an oligonucleotide, an antigen, an antibody, or combinations thereof having an affinity for a predetermined molecular target. In one embodiment, the predetermined molecular target is associated with a cancer cell, a leukemia cell, an acute lymphoblastic leukemia T-cell, or combinations thereof. In a particular embodiment, the ligand comprises an aptamer having an affinity for leukemia cells, e.g., an acute lymphoblastic leukemia T-cell. The aptamer may include any polynucleotide- or peptide-based molecule, for example. A polynucleotidal aptamer is a DNA or RNA molecule, usually comprising several strands of nucleic acids that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system. In one embodiment, the ligand comprises the DNA aptamer sgc8c having a sequence according to SEQ. ID No. 1:

5'-ATC TAA CTG CTG CGC CGC CGG GAA AAT ACT GTA CGG TTA GA-3'.

The DNA aptamer sgc8c has been shown to have a particular binding affinity for leukemia cells, e.g, acute lymphoblastic leukemia T-cells.

When the ligand comprises a hydrophilic dispersing agent, the hydrophilic dispersing agent may be directly or indirectly linked to respective ones of the quantum dots. In addition, when the ligand comprises a hydrophilic dispersing agent, the hydrophilic dispersing agent may comprise any compound that will increase a hydrophilicity of the nanoprobe relative to a nanoprobe without the hydrophilic dispersing agent. Exemplary hydrophilic dispersing agents include but are not limited to one or more of NAC (N-Acetyl-L-Cysteine (NAC), glutathione (GSH), PEG (polyethylene glycol), m-PEG, PPG (polypropylene glycol), m-PPG, PGA (polyglutamic acid), polysialic acid, polyaspartate, polylysine, polyethyeleneimine, biodegradable polymers (e.g., polylactide, polyglyceride), and functionalized PEG, e.g., terminal-functionalized PEG, and structural analogues of any of the above compounds.

In one embodiment, the hydrophilic dispersing agent is indirectly linked to respective ones of the quantum dots through a spacer or linking compound. For example, as will be explained below, in a particular embodiment, a NAC (N-Acetyl-L-Cysteine)-modified ethylenediamine ligand (NAC-EDA modified ligand) is first linked to the quantum dot surface via the sulfide groups of NAC. Thereafter, the surface amine groups provided by NAC-EDA may be reacted with an N-hydroxysuccinimide (NHS) ester derivative of methylpoly-ethylene glycol (MPEG-NHS ester) to improve overall dispersability of the nanoprobe.

In a particular embodiment, a plurality of hydrophilic dispersing agents are linked to a plurality of the Qdots so as to define a hydrophilic shell or coating for the nanoprobe. In one embodiment, a hydrophilic shell or coating is formed by linking a plurality of hydrophilic dispersing molecules to a plurality of Qdots surrounding the inorganic core. It is appreciated that other ligands may be attached to the Qdots as described herein, e.g., an active agent or a target agent, and that the hydrophilic shell or coating may not be continuous. Typically, the coating or shell will at least partially surround the inorganic core. In one embodiment, the hydrophilic dispersing agent comprises GSH. In another embodiment, the hydrophilic dispersing agent comprises NAC. As set forth in the Example, the present inventors have found that GSH and NAC are at least capable of coating a Qdot surface via conjugation through their sulfhydryl (—SH) groups, and thus form "hydrophilic Qdots" or "hydrophobic nanoprobes." Both GSH-Qdots and NAC-Qdots, and particularly NAC-Qdots, may be an attractive choice for the fabrication of activatable ("OFF/ON") Qdots for bioimaging and sensing applications.

When the ligand of the optically activatable nanoprobe comprises an active agent, the active agent may include any compound or composition that produces a preventative, healing, curative, stabilizing, ameliorative or other beneficial therapeutic effect. In a particular embodiment, the active agent is a STAT inhibitor, such as a STAT-3 inhibitor. Examples of mammalian STAT inhibitors include inhibitors of STAT-1, STAT-2, STAT-3, STAT-4, STAT-5a, STAT-5b, and STAT-6. In one embodiment, the active agent is one or more of BP-1-102, SF-1066 and S31-201, all of which have proven activity against STAT-3 with $IC_{50}$ values of 6.8, 35, and 86 μm, respectively.

STAT-3, in particular, is an oncogene constitutively activated in many cancer systems where it contributes to carcinogenesis. The signal transducers and activators of transcription (STATs) are a class of transcription factor proteins that regulate cell growth and survival. A total of seven STAT isoforms, encoded in distinct genes, have been identified in mammalian cells. STAT-3 protein isoform is known to directly up-regulate Bcl-xL, Mcl-1, cyclin D1/D2 and c-myc, contributing to compromised regulation by stimulating cell proliferation and preventing apoptosis in numerous human cancers including breast, prostate, melanoma, lung, brain, pancreatic, ovarian, colon cancers. STAT-3 activation occurs via phosphorylation of tyrosine 705, which promotes STAT dimer formation through STAT phosphotyrosine-SH2 domain interactions. These STAT dimers translocate to the nucleus, where they regulate gene expression. Constitutive STAT-3 activity mediates dysregulated growth and survival, angiogenesis, as well as suppresses the host's immune surveillance of tumors and represents a valid target for small molecule anti-cancer design. The STAT-3 inhibitor for use in the present invention may be any known inhibitor of STAT3 known in the art. Exemplary STAT3 inhibitors are disclosed in U.S. Published Patent Application Nos. 20100310645, 20090318367, 20090069420, 20080187992, 20070123502, 20050074502, and 20050004009, the entirety each of which is incorporated by reference herein. Typically, the STAT-3 inhibitor will include a sulfur-containing functional group, which may form a covalent disulfide bond with the Qdot to form a linkage between the STAT-3 inhibitor and the Qdot.

The optically activatable nanoprobes described herein may thus be utilized to monitor and/or treat any proliferation disorder characterized by the over-activation of a STAT protein. In one embodiment, the proliferation disorder to be treated is a cancer producing a tumor characterized by over-activation of STAT1, STAT3, STAT5, or a combination of two or all three of the foregoing. Examples of such cancer types include, but are not limited to, breast cancer, ovarian cancer, multiple myeloma and blood malignancies, such as acute myelogenous leukemia. In addition to cancer, the proliferation disorder to be treated using the compounds, compositions, and methods of the invention can be one characterized by aberrant STAT-3 activation within cells associated with a non-malignant disease, pathological state or disorder (collectively "disease"), and likewise comprising administering or contacting the cells with a an effective amount of one or more STAT3 inhibitors to reduce or inhibit the proliferation.

In still other embodiments, the active agent may include peptides (e.g., RGD peptide, integrin selective; see Dechantsreiter, M. A., et al., N-Methylated Cyclic RGD Peptides as Highly Active and Selective αvβ3 Integrin Antagonists. Journal of Medicinal Chemistry, 1999. 42(16): p. 3033-3040.), antibodies (e.g., CD10 monoclonal antibody for targeting human leukemia; see Santra, S., et al., Conjugation of Biomolecules with Luminophore-Doped Silica Nanoparticles for Photostable Biomarkers. Analytical Chemistry, 2001. 73(20): p. 4988-4993.) and proteins. When the optically activatable nanoprobes comprise a biologically active drug, as well a target-specific ligand, the disclosed nanoprobes are useful as target-specific drug delivery vehicles.

The imaging agent may comprise one or more of a fluorophore, iohexyl, and a paramagnetic chelate having a paramagnetic ion bound therein. In another embodiment, the imaging agent may be a fluorophore and/or a paramagnetic chelate (chelator) having an MRI (magnetic resonance imaging) contrast agent bound therein. The MRI contrast agent may comprise a paramagnetic ion selected from one or more of gadolinium, dysprosium, europium, and compounds, or combinations thereof, for example. In one embodiment, the paramagnetic ion comprises a gadolinium ion and the chelator is a DOTA-NHS ester (2,2',2"-(10-(2-(2.5-dioxopyrrolidin-1 yloxy)-2-oxoethyl)-14,7,10-tetraazacyclododecane-1,4,7-tryl)triaceticacid). $Gd^{3+}$ ions are paramagnetic and DOTA is a chelator of Gd ion. The Gd-DOTA is paramagnetic agent and it provides MRI contrast. Gd-DOTA is commercially available under the brand name ProHance® (also called Gadoteridol). In another embodiment, the imaging agent may comprise iohexyl.

In accordance with one aspect of the invention, the ligand(s) (e.g., a targeting agent, dispersing agent, and/or an active agent), the cross-linker or spacing compound, and/or the Qdot may be modified with a compound that increases the functionality and/or dispersability of the optically activatable nanoprobe in aqueous solutions, particularly at pH of 7.4. In one embodiment, the ligand(s) (e.g., a targeting agent, dispersing agent, and/or an active agent), the linking or spacing compound, and/or the quantum dot may be modified with NAC (N-Acetyl-L-Cysteine). NAC-modification of the Qdot, ligand, or linking/spacing molecules has several advantages: (i) NAC passivates the Qdot surface via formation of stable disulfide bonds, resulting in increased quantum efficiency; ii) NAC improves aqueous dispersability of the nanoprobes; and iii) NAC provides surface carboxyl groups for functionalization with other desired ligands.

The below description further describes exemplary embodiments of an optically activatable nanoprobe in accordance with the present invention and a method for making the same. It is understood that the present invention, however, is not limited to the below-described optically activatable nanoprobes, and that the nanoprobes may include one, two, or more of the ligands described below attached to the Qdots, may include other linked compounds, and may be further modified as necessary for the particular application.

In one embodiment, as shown in FIG. 1a, the optically activatable nanoprobe (MMCNP) comprises a super-paramagnetic iron oxide nanoparticle core (IONP; ~5-20 nm size) and satellite CdS:Mn/ZnS quantum dot (Qdots; ~3.5 nm size) shell. Each Qdot is attached to the core IONP by a heterobifunctional cross-linker molecule, dihydrolipoic acid (DHLA). The DHLA connects the IONP through its carboxyl end and to the Qdot via its bidentate thiol bonds. To minimize the possibility of cross-linking, the IONP-Qdot conjugation strategy involved controlled addition of DHLA modified IONP to unmodified Qdots as described in the Example below. The carboxyl and the thiol functional groups are compatible with the IONP and Qdot particle surfaces, respective[18,24-26].

Upon attachment of a Qdots to an IONP nanocrystal, a large surface area still remains available on the satellite Qdots for further surface modification and conjugation. Next, an N-Acetyl-L-Cysteine (NAC)-modified STAT3 inhibitor (NAC-STAT3; a therapeutic model drug), a NAC-modified folate (NAC-FA; a cancer targeting agent) and an NAC-modified ethylenediamine (NAC-EDA, an amine modified ligand) were separately synthesized. As set forth above, NAC-mediated surface modification of Qdots has several advantages: (i) it passivates the Qdot surface via formation of stable disulfide bonds, resulting in increased quantum efficiency, (ii) it improves aqueous dispersibility of Qdots, and (iii) it provides surface carboxyl groups for functionalization with other desired ligands. Furthermore, this approach reflects the uniqueness of the reported MMCNP design, where the separate synthesis of each of these ligands allows for control of the ratio of these ligands when attaching to Qdots or substitution of one of these ligands, resulting in a fully modular design of the MMCNP (akin to a nanoparticle LEGO®). After IONP-Qdot conjugation, further surface conjugation reactions were performed by treating IONP-Qdot with a mixture of NAC-STAT3, NAC-FA and NAC-EDA. The surface modification procedures are detailed in Examples below. The surface amine groups (provided by NAC-EDA) were reacted with the N-hydroxysuccinimide (NHS) ester derivative of methyl-poly-ethylene glycol (MPEG-NHS ester; a biocompatible highly-hydrophilic dispersing agent) to improve overall dispersibility of the MMCNPs.

A STAT-3 drug and folate (FA) were intentionally selected as electron-rich ligands that can substantially quench Qdot fluorescence. Substantial quenching typically refers to 75-100% quenching of fluorescence. In a more specific embodiment, substantial quenching refers to 90-100% fluorescence quenching. This selection process involved mixing of each of these ligands with Qdots followed by observation of the extent of luminescence quenching (data not shown). Each of these ligands thus serves a dual purpose. The treatment of IONP-Qdots with NAC-STAT3 and NAC-FA drastically reduced the fluorescence of the Qdots. It was noted that NAC itself did not quench Qdot luminescence, thus justifying the combined role of STAT-3 drug and FA as quenchers. As a result, the MMCNP is essentially in a fluorescently quenched ("OFF") state when the ligand(s) are attached to the Qdots. It is understood that by "OFF," however, it is not necessarily meant the nanoprobe is 100% quenched or does not exhibit some luminescence, but only that the amount of luminescence is greater when the ligand(s) are not attached vs. attached. The luminescence of the MMCNPs is restored ("ON" state) upon treatment with an appropriate cleaving agent, which effectively cleaves disulfide bonds between the ligand and the IONP-Qdots, such as glutathione (GSH).

Figure 1B:
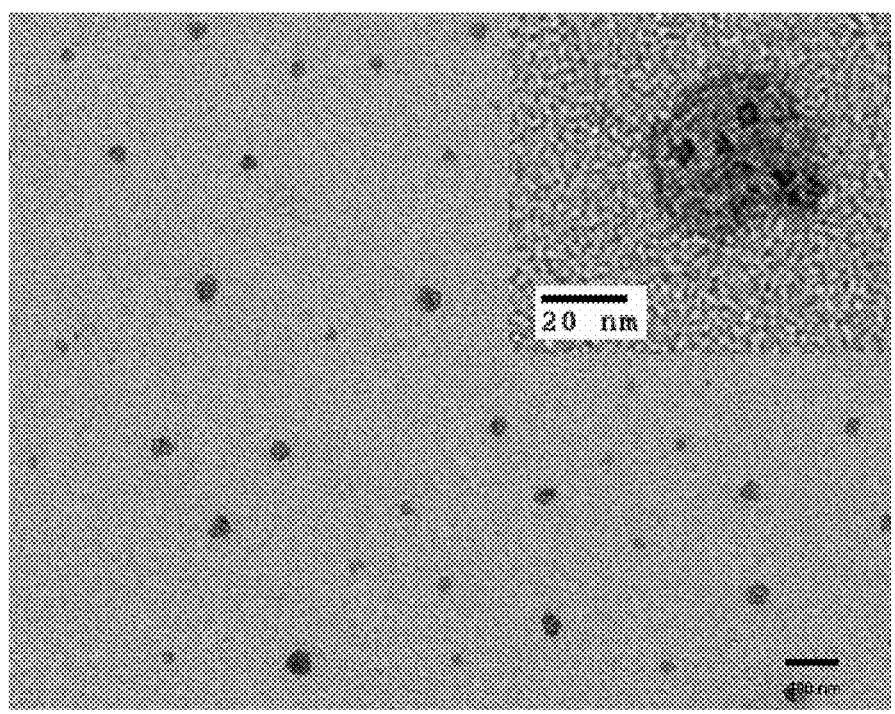
FIG. 1b is a TEM image of various activatable multifunctional/multimodal composite nanoprobes (MMCNPs) showing nearly spherical particles with irregular surface morphology indicative of the presence of satellite quantum dots (Qdots) on the IONPs (iron oxide nanoparticle core). The size of the MMCNPs ranges from 20 nm to 40 nm, due to polydispersity of IONPs. The inset shows a high magnification TEM image of a single MMCNP. The IONP can be discerned in the image by its light grey contrast while the Qdots appeared with dark contrast on the IONP surface.
Figure 7:
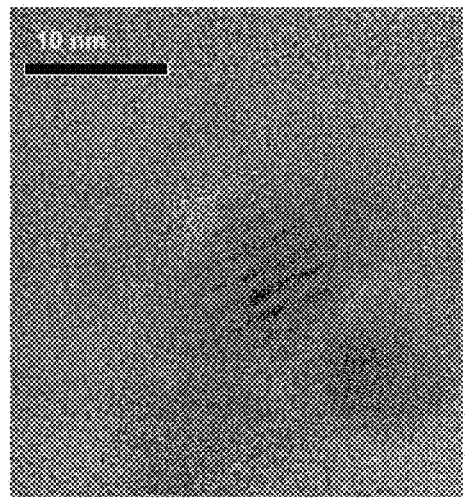
FIG. 7 is a high resolution TEM (HRTEM) image of a single MMCNP. Individual satellite Qdots on the IONP surface can be clearly identified by their single crystalline structure while the IONP (iron oxide nanoparticle core) in the HRTEM image is obscured by the satellite Qdots.

The morphological, optical, and magnetic properties of MMNCPs were extensively characterized. TEM studies confirm the formation of about 20-40 nm size nanocomposites as shown in FIG. 1b. The IONP core and satellite Qdots surrounding the core are clearly visible with low resolution TEM (FIG. 1b), whereas magnified TEM images clearly show Qdots around the IONP (FIG. 1b inset). HRTEM also confirms the single crystalline structure of the Qdots (FIG. 7) surrounding the core IONP. Inductively coupled plasma analysis of the sample confirms the presence of Zn (about 41 wt %), Fe (about 6.2 wt %) and Cd (about 10 wt %) with a relative ratio of about 6.6:1.0:1.6 (WAN). Zeta potential ($\xi$) measurements correlate with particle surface charge. The $\xi$ values of IONP, IONP-DHLA, IONP-Qdots-STAT3-FA and IONP-Qdot-STAT3-FA-m PEG are about −20 mV, about −4.0 mV, about −17 mV and about −21 mV, respectively. As expected, DHLA modification of the iron oxide nanoparticle core (IONP) drastically reduced its surface charge due to reduction of the negative surface charge of the IONP. Further surface modification with the STAT-3 drug and folic acid (folate) resulted in an increase in the overall negative surface charge on the particle. This is likely due to the presence of carboxyl groups on the folate residues on the particle surface.

Figure 8:
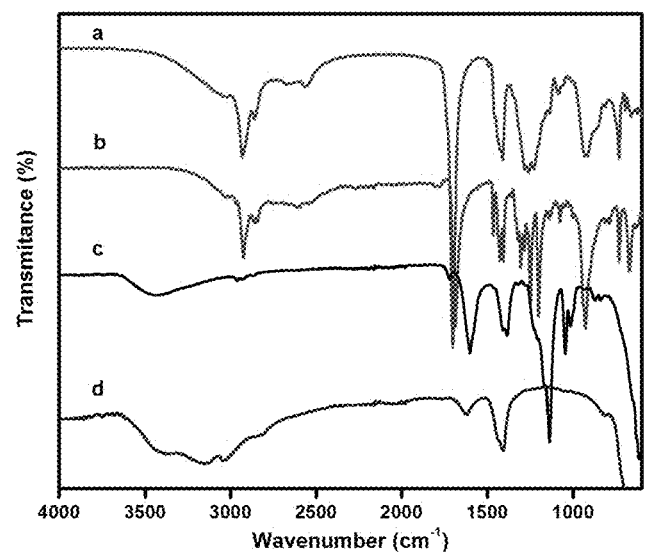
FIG. 8 shows FT-IR spectra of (a) dihydrolipoic acid, (b) lipoic acid, (c) dihydrolipoic acid coated IONPs, and (d) IONPs. The broad band at 3200-3600 cm-1 indicates the surface hydroxyl group of the super paramagnetic IONPs (Figure S4d). The bands at about 3046 (O—H), about 2934 (—CH2-), about 1697 (C=O), about 1252 (O—H), and about 935 (OH) $cm^{-1}$ were observed for dihydrolipoic acid and lipoic acid in (a) and (b) respectively. The presence of these characteristic bands into the spectra of dihydrolipoic acid coated IONPs (c) confirmed the dihydrolipoic acid coating on the surface of IONPs.

Pegylation with biocompatible mPEG, however, showed minimal effect on the particle surface charge due to its neutral nature. It was observed that pegylated particles exhibited good phosphate buffer dispersibility. A comparative analysis of FT-IR spectra of dihydrolipoic acid (DHLA) (a), lipoic acid (b), DHLA-coated IONPs (c), and IONPs (d) confirmed successful surface modification of IONP with DHLA (FIG. 8). Fluorescence spectroscopy in solution was used to investigate the Qdot luminscence properties at different stages of MMCNP development as well as for tracking the drug release events.

Figure 9:
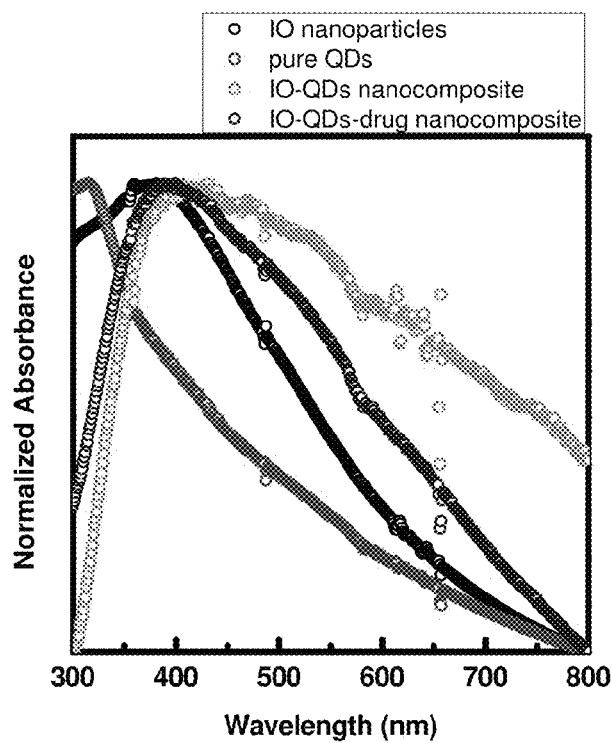
FIG. 9 shows normalized UV-Vis absorbance spectra of pure Qdots (red), IONP (black), Qdots attached to IONP (green) and MMCNPs (blue). After Qdots are attached to IONPs, a large red shift of the absorption spectrum is observed, indicating successful attachment of satellite Qdots to IONP core. The attachment of STAT-3 to form MMCNPs leads to a narrowing of the UV-Vis spectrum and the slight blue shift in comparison to IONP-Qdot construct.
Figure 10:
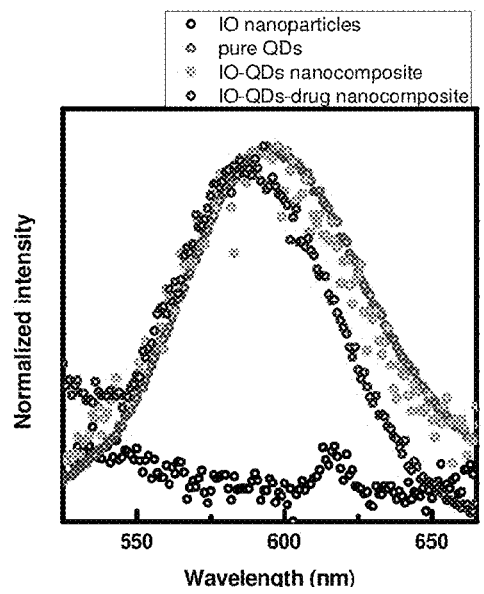
FIG. 10 shows a normalized emission spectra of pure Qdots (red), IONP (black), Qdots attached to IONP (green) and MMCNPs (blue). Only a blue shift of the MMCNPs with respect to the free Qdots and the IONP-Qdot construct is observed.

Glutathione (GSH), a tripeptide biomolecule found in all animal cells at relatively high cytosolic concentration (about 1-10 mM[27,28], reduced form), effectively reduces disulfide bonds and in this process glutathione is converted to glutathione disulfide (GSSG), its oxidized form.[29] The design of the MMCNPs is such that once they are exposed to an intracellular GSH environment, the nanoprobes will break apart into its different constituents that make up the composite nanoprobes. This forms the basis of the intracellular tracking of the STAT-3 drug release as schematically shown in FIG. 1a. Distinct changes in absorption spectra were observed for IONP-Qdot and IONP-Qdot-STAT3 conjugates in comparison to Qdots (FIG. 9). The Qdot absorption spectrum broadens significantly and slightly shifts towards longer wavelength when conjugated to IONPs. However, upon further conjugation with NAC-STAT3 drug, NAC-FA and NAC-EDA, a decrease in spectral width along with slight blue shift was observed with respect to the IONP-Qdots conjugates. Such changes in absorption spectral characteristics support successful surface conjugation of Qdots with IONP, STAT3 drug and FA. The emission of MMCNP is slightly blue shifted compared to either Qdots or IONP-Qdot conjugates (FIG. 10).

Figure 2A:
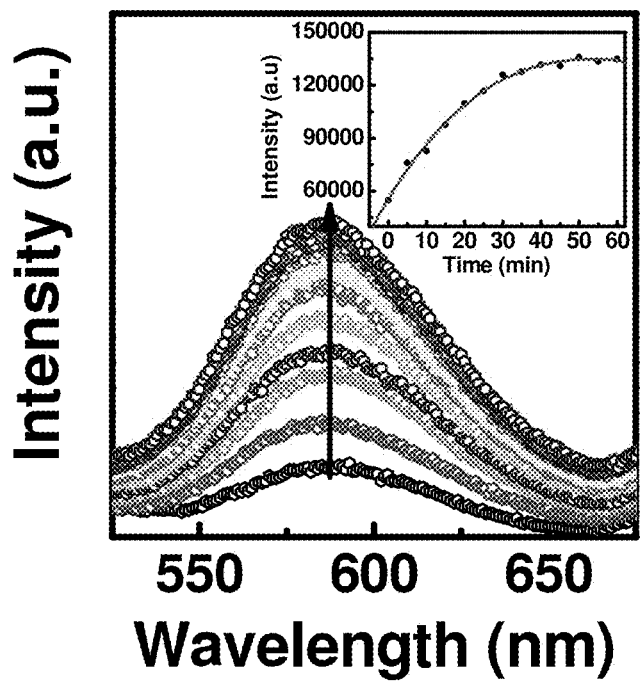
FIG. 2a shows a Qdot fluorescence emission spectra (excitation wavelength: 375 nm) measured as a function of time at 7.0 mM glutathione (GSH) concentration. These data show that full restoration of Qdot fluorescence occurs within one hour, after which no further increase in Qdot fluorescence intensity is observed. The inset shows a plot of Qdot fluorescence intensity measured at the peak emission wavelength (582 nm) as a function of time. This plot illustrates that the fluorescence intensity plateaus at 60 minutes. The (red) line of the plot is a non-linear fit to the data.
Figure 2B:
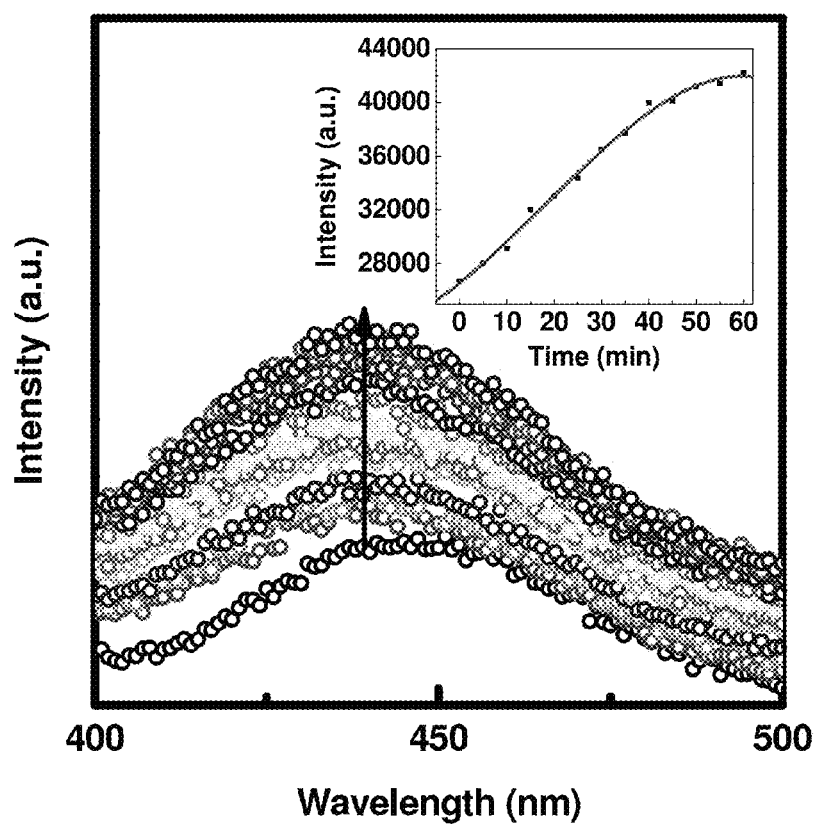
FIG. 2(b) shows a STAT-3 fluorescence emission spectra (excitation wavelength: 300 nm) measured as a function of time at 7.0 mM GSH concentration. These data show that full restoration of STAT-3 fluorescence occurs within one hour, after which no further increase in STAT-3 fluorescence intensity is observed. The inset shows a plot of STAT-3 fluorescence intensity measured at the peak emission wavelength (430 nm) as a function of time. This plot illustrates that the fluorescence intensity plateaus at 60 minutes. The (red) line of the plot is a non-linear fit to the data.
Figure 11:
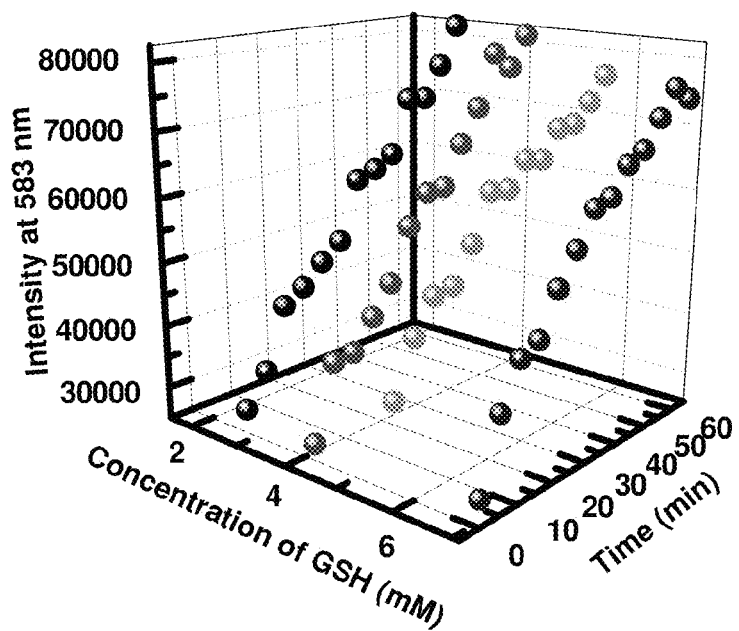
FIG. 11 shows a 3D plot of the Qdot fluorescence intensity recovery from MMCNP ("OFF state") as a function of time for GSH concentrations of about 2.8, about 4.2, about 5.7, and about 7.0 mM. Even at the lowest GSH concentration, the Qdot fluorescence recovers in approximately 1 hour. Furthermore, the timescale of fluorescence recovery appears to be independent of GSH concentration higher than about 1.4 mM. Since the intra-cellular concentration of GSH ranges from about 1 mM to about 15 mM, it is expected that MMCNP uptaken by the cancer cells will release its cargo intracellularly (e.g., drug) within about an hour.

Fluorescence data acquired by adding GSH to MMCNPs in solution show that Qdot fluorescence can be substantially restored in less than one hour (FIGS. 2a and 2b). Furthermore, a systematic study on the effect of GSH concentration on the time scale of fluorescence restoration shows that there is no significant effect of varying GSH concentrations in the range of 2.8 mM to 7 mM (FIG. 11). The observed spectral features of the "ON" state Qdots (i.e. after release from MMCNP) (FIG. 2a) are in good agreement with those of Qdots in solution as shown in FIG. 10. The STAT-3 inhibitor is also a fluorescent molecule ($\lambda_{ex}$: 300 nm and $\lambda_{em}$: 396 nm) of which the fluorescence is substantially quenched in MMCNPs. Fluorescence quenching of STAT-3 drug is presumably due to electron/energy transfer from STAT-3 to Qdots. It is unlikely that the IONP will have any significant contribution towards STAT-3 fluorescence quenching as STAT-3 is not directly attached to IONP surface. Restoration of STAT-3 drug emission is observed once MMCNPs are treated with GSH in solution (FIG. 2b), thus confirming disintegration of MMCNPs and release of STAT-3 inhibitors.

To confirm the effectiveness of the optically activatable nanoprobes (MMCNPs), the MMCNPs were challenged against the intracellular GSH environment where the reported GSH concentration is in the millimolar (mM) range, typically between about 2 mM and about 15 mM[27,28]. The human breast cancer (MDA-MB-231) cell line, known to over-express folate receptors[30], and the mouse thymus stromal epithelial cell line (TE-71) were incubated for up to 24 hrs with MMCNP at a concentration of about 50 µg/mL. As expected, a significant uptake of folate conjugated MMCNPs by the cancer cells was observed compared to normal cells as shown in FIG. 3. These results also show that substantial restoration of fluorescence occurs within 3 hr incubation. Restoration of fluorescence in cancer cells is a direct confirmation of targeted cellular uptake of MMCNPs and subsequent dispersal of MMCNPs into its separate components, e.g., IONP, Qdots, and the release of ligands, including drug molecules.

Figure 4A:
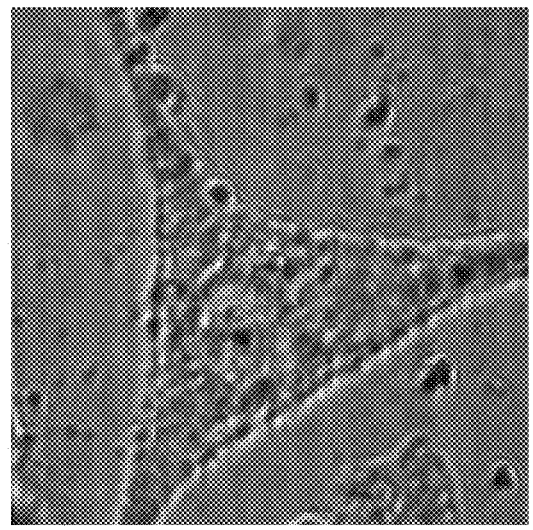
FIGS. 4a-4c shows: (a) bright field; and (b) corresponding epi-luminescence laser microscopy images of MDA-MB-231 cells incubated with MMCNPs for 5 hours. The bright spots in the fluorescence image indicate the location of aggregated Qdots, revealing that the MMCNPs have reacted with intra-cellular GSH. After this reaction, the GSH coated Qdots are somewhat hydrophobic in nature leading to aggregation in the intra-cellular environment. Most of the aggregates as they appear in the bright field image (dark spots) and fluorescence image (corresponding bright spots) are localized near the cell membrane because of their hydrophobic nature. (c) Normalized ensemble fluorescence emission spectra acquired by sample scanning laser confocal microscopy under 375 nm laser excitation. The ensembles are constructed by averaging fluorescence emission spectra obtained at different locations inside individual cells under illumination with a diffraction limited laser spots (~300 nm). Spectra were acquired at the location of the Qdot aggregates (red line) and the cellular regions without Qdots (autofluorescence, dark cyan line). As a control, the same experiment was completed for Qdots in the "OFF state" (black line) and "ON state" (blue line) on glass substrates. Both the intra-cellular and extra-cellular "ON state" Qdots appear slightly red shifted with respect to the "OFF state" Qdots. In addition, the "ON state" Qdots are significantly broadened at the blue edge as well as the red edge of the spectra, possibly due to the presence of GSH on the Qdot surface. The difference in the appearance of the red shoulders in the intra-cellular and extra-cellular "ON state" Qdots is most likely due to the difference in the environment. The spectral feature around 500 nm in the intra-cellular "ON state" Qdot fluorescence emission ensemble spectrum is due the contribution of cellular autofluorescence.
Figure 4B:
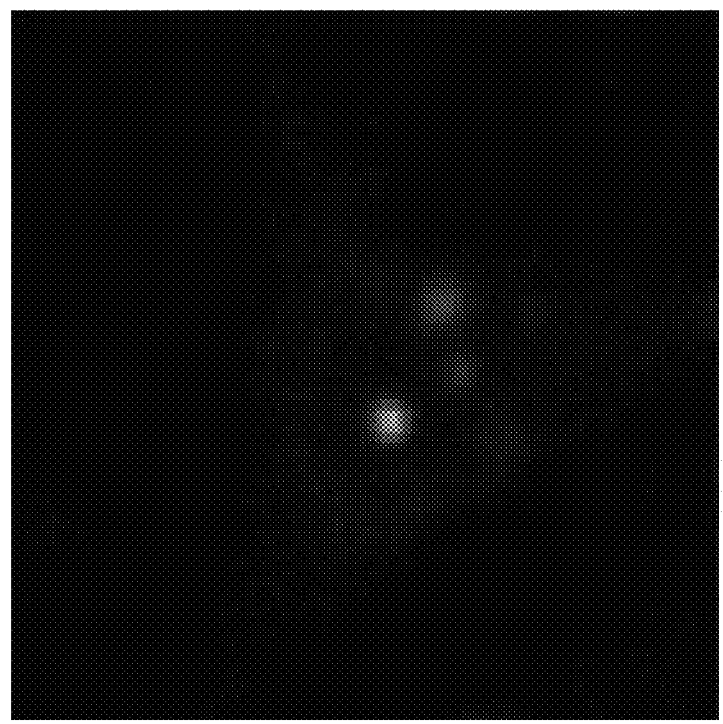
Figure 4C:
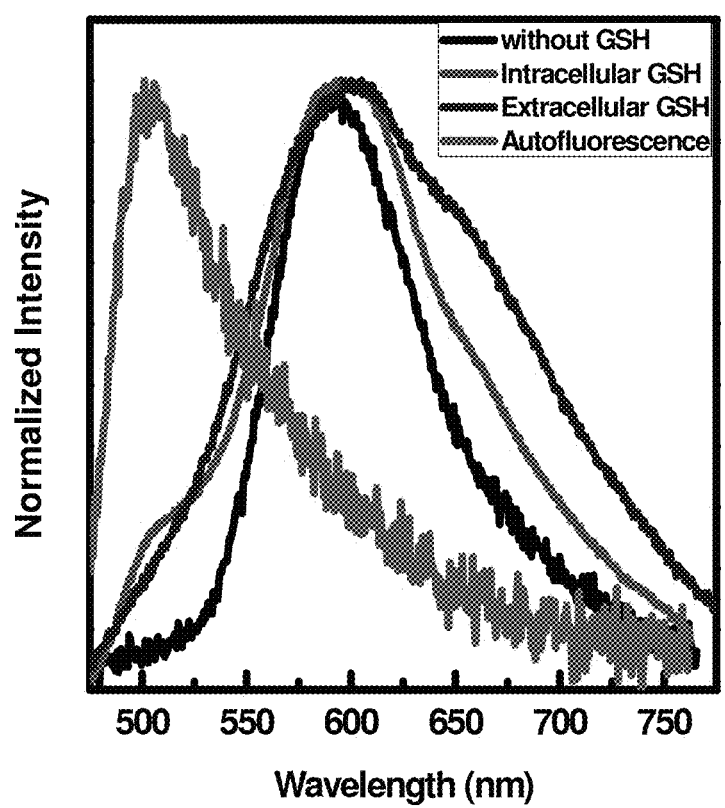

Systematic optical studies were performed to investigate intracellular drug release at the single cell level. Confocal microscopy images of the MDA-MB-231 cells incubated with MMCNPs for 5 hrs (FIGS. 4a-4c) clearly show that MMCNPs were uptaken by the cells. In addition, strong fluorescence signal from only a few locations in the cell can be observed. These data show that Qdots were released from the MMCNP through the cleavage of disulfide bonds by GSH (see FIG. 1a). Besides the images of single cells incubated with MMCNPs, emission spectra of different regions in single cells were also collected (FIG. 4c, red and cyan lines).

The Qdots in the intracellular environment show emission spectra that are red-shifted and broadened with respect to uncoated free Qdots in solution (FIG. 10). These spectral differences are attributed to aggregation of the Qdots after release from MMCNP in the cytosol. This observation was confirmed with solution experiments on bare Qdots by observing emission spectra before and after aggregation, as well as addition of GSH to each of these samples (data not shown).

It was found from control experiments that addition of GSH to a suspension of bare Qdots leads to a stable Qdot suspension and has no noticeable effect on the Qdot emission properties (data not shown). These observations may provide preliminary indication that in the intracellular environment GSH does not necessarily exchange with the NAC/cargo-ligand that is initially present on the Qdot surface due to the fact that intracellular Qdot aggregation is observed after cargo release, although it could be argued that binding constants of both molecules could be comparable given that GSH and NAC both contain a single thiol group in their structure (monodentate ligand).

The observation of only a few bright spots in a single cell in the fluorescence images indicates aggregation of multiple Qdots in a single or a few clusters. The Qdot aggregation is reasonable given that while in the MMCNP, Qdots are stabilized by PEG. After exposure to GSH, the PEG is removed by cleavage of disulfide bonds, resulting in hydrophobic Qdots that self-aggregate. In addition, the data shows that these Qdot aggregates preferentially localize near the cell membrane, again due to their hydrophobic nature. Other locations where Qdot aggregates are not present only show autofluorescence. It should be noted that while the STAT3 drug itself is typically also fluorescent (FIG. 2b), experiments on intracellular delivery cannot be reliably performed by measuring the STAT3 drug fluorescence due to weak fluorescence and the presence of cellular auto-fluorescence, hence the need for the optical signal of the Qdots.

Figure 13:
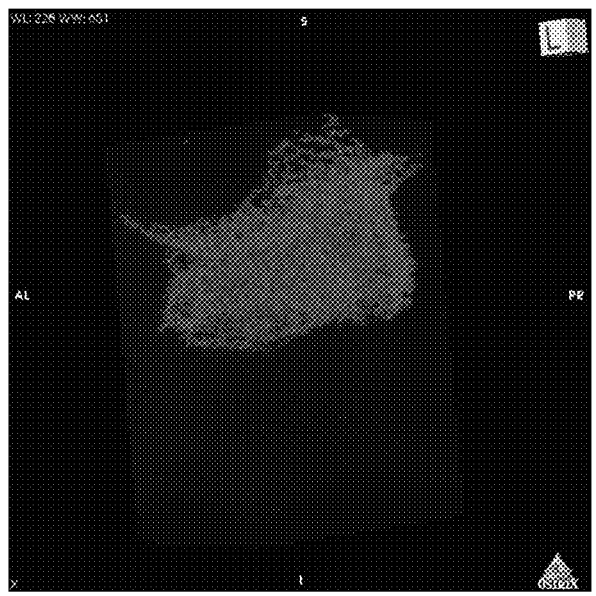
FIG. 13 is a 3D reconstruction of MRI images recorded on agar phantom. This demonstrates the appearance of strong MRI signal from the MDA-MB-231 cells loaded with the MMCNPs (indicated with false red color).

To demonstrate the concept of multimodality of the MMCNPs, an agar phantom was prepared using a 10 mm NMR tube (FIGS. 5a-5d) for MRI and optical imaging studies. FIG. 5a shows the schematic of agar phantom design. The bottom part of the tube contains only MDA-MB-231 cells (as a control), middle part contains only MMCNPs (as a control) and the top part of the tube contains the same cells loaded with MMCNPs. All of these were dispersed in 3% agarose gel under same condition. A digital image of the tube was recorded under room light (FIG. 5b) as well as under illumination by a hand-held 366 nm multiband UV lamp (FIG. 5c). The unfiltered images clearly show a light brown color where cells are located in room light conditions whereas an intense red color appears due to Qdot fluorescence under UV illumination. The MDA-MB-231 cells loaded with the MMCNPs emit red fluorescence that is clearly visible to the naked eye. Control cells do not show any detectable fluorescence emission. An MRI image of the phantom (FIG. 5d) clearly shows cell clusters that correlate well with the fluorescence image. A 3D reconstruction of the MR images is provided in FIG. 13. This demonstrated the appearance of strong MRI signal from the MDA-MB-231 cells loaded with the MMCNPs (indicated with false red color) in contrast with the control cells.

A CyQUANT™ cell proliferation assay was used in a comparative cell viability study to determine cytotoxicity of MMCNPs without STAT-3 drug (control particle), STAT-3 drug itself, and MMCNPs with STAT-3 conjugation. Two cancer cell lines, MDA-MB-231 and pancreatic (Panc-1) cancer cells were used along with mouse thymus stromal epithelial TE-71 cells (control). Results (shown in FIG. 6) suggest that MMCNPs (with STAT-3) treated cancer cells have lower viability than cells treated with free STAT-3 drug when MMCNPs and STAT-3 were administered to the cell medium at identical concentrations. This finding is highly significant given that free STAT3 drug alone in medium is in high excess compared to STAT-3 drug present in MMCNPs under these conditions. Even though the MMCNPs consume much less STAT3 drug, the delivery efficiency is dramatically increased, thus resulting in increased therapeutic efficiency while minimizing the potential for medical side effects due to presence of excess free drug.

In view of the above, a new and unique quantum dot (Qdot)-iron oxide (IO) based multimodal/multifunctional nanocomposite probe that is optically and magnetically imageable, targetable and capable of reporting on intracellular drug release events has been described herein. By design, the present nanoparticle system has multimodalities (optically and magnetically active) and multifunctionalities (i.e. imaging, targeting, drug delivery) that are current state-of-the-art in nanomedicine research[1,8,10,14-16,18,23-26]. In addition, the MMCNP discussed here integrate sensing modalities that report on the event as well as the location of intra-cellular release of cargo (drug, etc.). The impact and implications of this new development along with the traditional multimodalities and multifunctionalities are immediate for drug discovery and cancer biology.

In accordance with another aspect, there is provided a method for monitoring intracellular drug delivery within a subject using any embodiment of an optically activatable nanoprobe described herein. In one embodiment, the method comprises administering to the subject an effective amount of a nanoprobe comprising an inorganic core and a plurality of quantum dots linked to the inorganic core. A ligand comprising at least an active agent is linked to respective ones of the plurality of quantum dots. Upon intracellular uptake of the nanoprobe, the linkage between the active agent and the ligand is cleaved to allow release of the active agent and to allow the plurality of quantum dots to transfer from a quenched state, wherein the luminescence of the plurality of quantum dots is quenched, to a luminescent state, wherein the luminescence of the plurality of quantum dot is activated. In one embodiment, the linkage between the bioactive agent and the quantum dot is cleavable by intracellular glutathione (GSH).

In a particular embodiment, the ligand may further comprise a targeting agent and a hydrophilic dispersing agent. For example, the active agent may comprise a STAT3 inhibitor, the targeting agent may comprise folate, and the hydrophilic dispersing agent may comprise m-polyethylene glycol (mPEG) or derivatives thereof. In addition, optionally, the bioactive agent, targeting agent, and the hydrophilic dispersing agent may be modified with N-Acetyl-L-Cysteine to provide improved dispersability of the nanoprobes and additional functional groups for the attachment of desired ligands.

In addition, the above-described method may further comprise the step of detecting a presence of the plurality of quantum dots, wherein an increase in luminescence of the quantum dots is indicative of a release of the active agent intracellularly. The detecting may be done by any suitable detection method known in the art appropriate for the particular type of Qdot. For example, the detection may be done by any one or more of transmission electron microscopy (TEM), scanning electron microscopy (SEM), dynamic light scattering (DLS), UV-visible (UV-VIS) spectroscopy, Fourier transform infrared spectroscopy (FTIR), zeta potential, high pressure liquid chromatography-mass spectrometry (HPLC-MS), NMR/IR, mass spectrometry (MS), fluorescence excitation and emission spectroscopy and fluorescence microscopy, near infrared (NIR) imaging (NIRS), and magnetic resonance (MR) imaging and spectroscopy The administering to the subject, who may be any mammalian subject, may be done according to any suitable route of in vivo administration that is suitable for delivering the composition into the subject. The preferred routes of administration will be apparent to those of skill in the art, depending on the medium, the targeting agent (if present) or the active agent. Exemplary methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue.

In accordance with another aspect, there is provided a method for making optically activatable nanoprobes as described herein. The method comprises obtaining a plurality of nanoparticles comprising an inorganic core, e.g., iron oxide core; obtaining a plurality of quantum dots; linking the plurality of quantum dots to the inorganic core; and linking at least one ligand to respective ones of the plurality of quantum dots, wherein the at least one ligand comprises an active agent, a targeting agent, or a hydrophilic dispersing agent. In a particular embodiment, the at least one ligand comprises an active agent, a targeting agent, and a hydrophilic dispersing agent. As discussed above, the active agent may comprise a STAT-3 inhibitor, the targeting agent comprises folate, and the hydrophilic dispersing agent comprises polyethylene glycol (e.g., mPEG).

Further, in one embodiment, the method further comprises providing a coating of dihydrolipoic acid (DHLA) about the inorganic core to connect/link the Qdots to the iron oxide core. In some embodiments, the method further comprises modifying at least one of the active agent, the targeting agent, and the hydrophilic dispersing agent with N-Acetyl-L-Cysteine to increase dispersability and multifunctionality of the nanoprobe. A specific process for making optically activatable nanoprobes as described herein is set forth in the example below.

In accordance with another aspect of the present invention, there is provided another embodiment of a multi-modal, multi-functional nanoparticle (hereinafter DNCP or DNCPs) that allows for enhanced in vivo efficacy of active agents, as well as allows for the improved non-invasive in vivo bio-imaging. In one embodiment, the DNCPs comprise an optically activatable nanoprobe having a core component. In this embodiment, the core component comprises a quantum dot core and at least one ligand linked to the quantum dot core. In this embodiment, the DNCPs differ from the above-described nanoparticles in that the Qdot itself comprises the nanoparticles' core rather in contrast to the inorganic core described above having a plurality of satellite Qdots surround an inorganic core. A number of different chemical entities may be linked to the DNCPs, such as active agents, imaging agents, and targeting agents according to the same structures and methods described above.

In one embodiment, at least one active agent, e.g., a NAC-modified STAT3 inhibitor, is linked to the Qdot core by a disulfide bond, for example. In this way, when the STAT3 inhibitor is linked to the Qdot core, the STAT3 drug attachment to the Qdot surface will substantially quench Qdot fluorescence. The restoration of Qdot fluorescence will take place when intracellular GSH acts upon the DCNP, cleaving the disulfide bond and releasing STAT3 drug from the DNCP core into the cytosol. Restoration of fluorescence typically involves at least a noticeable increase of fluorescence from a substantially quenched state.

In one embodiment, a chitosan-based shell surrounds the Qdot core and any chemical entities attached thereto in the DCNPs. In one embodiment, the chitosan-based shell comprises a chitosan polymer and a hydrophilic dispersing agent. Chains of the chitosan polymer electrostatically interact with chains of the hydrophilic dispersing agent to form an entangled network comprising the chitosan polymer and the hydrophilic dispersing agent. While not wishing to be bound by theory, it is believed that the chitosan-based shell will effectively scavenge ion leakage, e.g., cadmium ion leakage, from the Qdot core by forming a metal-ligand complex and will passivate cytotoxicity. When a plurality of active agents (e.g., a STAT-3 inhibitor) are attached to the Qdot core, the plurality of active agents may be released intracellularly upon cleavage of the bond between the active agents and the Qdot core.

The hydrophilic dispersing agent of the chitosan-based shell may be any compound having repeating structural units that have one or more functional groups that will interact by electrostatic or charge attraction (or otherwise) with the amine functional groups of the chitosan polymer. In one embodiment, the hydrophilic dispersing agent is a polymer other than chitosan having repeating structural units, wherein each of the structural units includes one or more carboxyl groups. In a particular embodiment, the hydrophilic dispersing agent comprises polyglutamic acid (PGA) or any structural analogues or derivatives thereof. The advantages of utilizing PGA as the hydrophilic dispersing agent include the fact that PGA is a negatively charged biocompatible and biodegradable natural polymer, rendering it suitable for in vivo applications. Similarly, PGA increases the overall hydrophilicity of the chitosan-based nanoparticles, thus improving the stability of the nanoparticles having PGA therein at physiological pH conditions (e.g., pH 7.4). Further, PGA provides additional functional groups to incorporate additional functionality and/or modalities to the nanoparticles, such as the attachment of imaging agents, targeting agents, and/or further active agents to the nanoparticles. Even further, the incorporation of PGA in the nanoparticles will reduce the positive surface charge on each of the nanoparticle's surface (relative to a chitosan-based nanoparticle without the PGA), which will likely aid in reducing non-specific uptake by cells.

Alternatively, the hydrophilic dispersing agent may comprise or further comprise any other compound that will increase the hydrophilicity of the DNCPs relative to a nanoparticle without the hydrophilic dispersing agent. In other embodiments, for example, the hydrophilic dispersing agent may comprise one or more of NAC, glutathione, PEG (polyethylene glycol), m-PEG, PPG (polypropylene glycol), m-PPG, polysialic acid, polyaspartate, polylysine, polyethyeleneimine, biodegradable polymers (e.g., polylactide, polyglyceride), and functionalized PEG, e.g., terminal-functionalized PEG, analogues, derivatives, or combinations thereof of the above compounds. Optionally, a cross-linking compound may be provided to conjugate the amine groups of the chitosan polymer and the carboxyl groups of the hydrophilic dispersing agent together.

The at least one ligand linked to the Qdot may comprise an active agent, a targeting agent, a hydrophilic dispersing agent, an imaging agent, any other desired compound, and combinations thereof. In one embodiment, the biologically active agent, targeting agent, and/or imaging agent are linked to the Qdot core via thiol groups on the Qdot surface. In another embodiment, the biologically active agent, targeting agent and/or imaging agent may be linked to the chitosan-based shell, e.g., to either or both of the chitosan polymer and the hydrophilic dispersing agent. It is contemplated that the additional ligands described herein may be linked to the chitosan polymer by bonding, covalent or otherwise, through the amine groups of the chitosan polymer, although the invention is not so limited. When the chitosan-based shell comprises PGA, the respective ligand may be bonded to the hydrophilic dispersing agent through compatible functional groups on the hydrophilic dispersing agent. For example, when the hydrophilic dispersing agent is PGA, the additional ligand may be bonded to the PGA polymer through its amine or carboxyl functional groups. In some embodiments, spacer molecules or coupling agents may be utilized between the ligand to be attached and the chitosan polymer or the hydrophilic dispersing agent to provide the linkage between the ligand and the other substrate.

Figure 15:
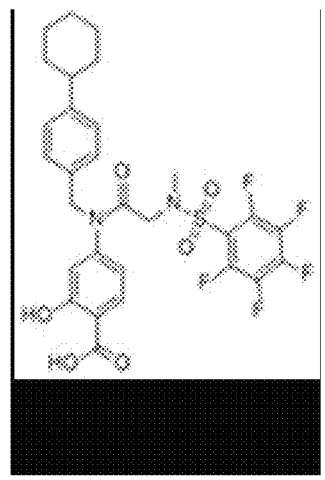
FIG. 15 shows a plurality of STAT3 inhibitors for use with nanoparticles in accordance with an aspect of the present invention.
Figure 16:
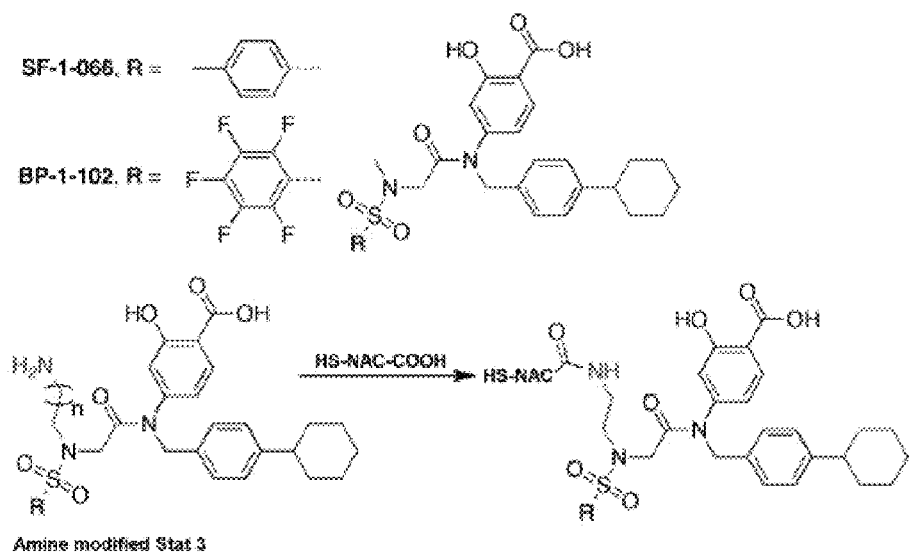
FIG. 16 illustrates an exemplary NAC-modified STAT3 inhibitor.

The active agent, imaging agent, hydrophobic dispersing agent, and the targeting agent may be any compound as described or defined herein. Further, in any embodiment, the active agent, imaging agent, hydrophobic dispersing agent, and the targeting agent may be activatable as define herein. In one embodiment, the active agent is a STAT3 inhibitor, such as one or more of BP-1-102, SF-1066 and S31-201, all of which have proven activity against STAT3 with $IC_{50}$ values of 6.8, 35, and 86 µm, respectively. FIG. 15 shows the structure of BP-1-102, for example. As mentioned above, the STAT3 inhibitor may be NAC-modified. FIG. 16 illustrates an exemplary NAC-modified STAT3 inhibitor.

The imaging agent may comprise one or more of a fluorophore, iohexyl, and a paramagnetic chelate having a paramagnetic ion bound therein. In one embodiment, either or both of the hydrophilic dispersing agent and the chitosan polymer may be labeled with a fluorophore. In another embodiment, either or both of the hydrophilic dispersing agent and the chitosan polymer may be labeled with a fluorophore and also a paramagnetic chelate (chelator) having an MRI (magnetic resonance imaging) contrast agent bound therein linked to the chitosan polymer so that the recovered stabilized chitosan-based nanoparticles are effective as a bimodal agent that is fluorescent as well as paramagnetic. The MRI contrast agent may comprise a paramagnetic ion selected from one or more of gadolinium, dysprosium, europium, and compounds, or combinations thereof, for example. In one embodiment, the paramagnetic ion comprises a gadolinium ion and the chelator is a DOTA-NHS ester (2,2',2''-(10-(2-(2.5-dioxopyrrolidin-1-yloxy)-2-oxoethyl)-14,7,10-tetraazacyclododecane-1, 4,7-tryl)triaceticacid). $Gd^{3+}$ ions are paramagnetic and DOTA is a chelator of Gd ion. The Gd-DOTA is paramagnetic agent and it provides MRI contrast. Gd-DOTA is commercially available under the brand name ProHance® (also called Gadoteridol). In another embodiment, either or both of the chitosan polymer or the hydrophilic dispersing agent may be solely or additionally linked with iohexyl such that the recovered nanoparticles are radio-opaque.

Figure 14:
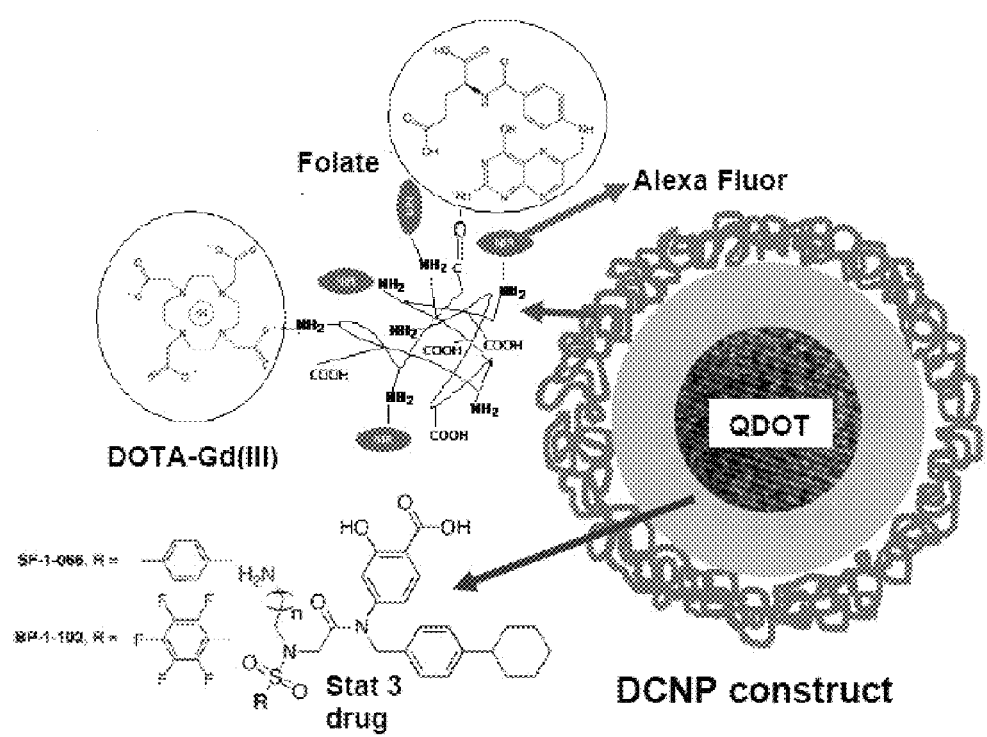
FIG. 14 shows another embodiment of an optically activatable nanoprobe (DNCP) in accordance with an another aspect of the present invention.

A particular embodiment of a DNCP having a Qdot core and a chitosan-based shell is shown in FIG. 14. It is appreciated that the illustrated embodiment is merely exemplary and that the nanoparticles may include more or less chemical entities than shown, or may comprise entirely different chemical entities. In the illustrated embodiment, the DNCP comprises a Qdot core, which may be any quantum dot material as described above, such as CdS:Mn/ZnS or ZnS:Mn/ZnS. To the Qdot surface, there is attached a N-acetylcysteine (NAC)-modified STAT-3 inhibitor. N-acetylcysteine acts a Qdot surface passivator, as well as a linker between the STAT-3 inhibitor and the Qdot core through its carboxyl and/or thiol groups.

The chitosan-based shell comprises chitosan polymer (commercially available; had a measured molecular weight=approximately $5.3 \times 10^5$ Da; a degree of acetylation=77) and PGA (commercially available, MW approximately 4130 Da, biocompatible/biodegradable). The chitosan polymer includes a plurality of amine groups, which will interact by electrostatic or charge attraction (or otherwise) with the carboxyl groups of the PGA to form an entangled network of the two polymers. In the embodiment shown, the PGA and chitosan polymer are cross-linked using a water-soluble carbodiimide cross-linker (1-Ethyl-3-(3-dimethylaminopropyl)carbodiimide) (EDC). Alternatively, any other cross-linking compound may be utilized. EDC coupling conjugates the amine groups of the chitosan polymer and the carboxyl groups of the PGA together forming an amide bond.

In the illustrated embodiment of FIG. 14, two imaging agents (Alexa Fluor® 660 and Gd-DOTA) are bonded to the chitosan polymer. Alexa Fluor® 660 is a commercially available, amine-reactive, near infrared (NIR)-emitting fluorescent dye (MW approximately 1300; wavelength of absorption and emission band maxima are 663 nm and 690 nm, respectively; molar extinction coefficient 132,000 cm-1 M-1). Gd-DOTA is a commercially available amine-reactive paramagnetic Gd-chelate complex, which is typically used as a MRI T1 contrast agent. In addition, to the chitosan polymer, there is bonded a folate targeting agent having both amine and carboxyl functional groups.

In one embodiment, the DNCPs of FIG. 14 may be synthesized by forming three different W/O microemulsions (ME-I, ME-II and ME-III). Each microemulsion comprises an oil, a surfactant, and an aqueous phase having a chitosan polymer. Each microemulsion, however, includes a different aqueous phase. The ME-1 aqueous phase comprises Qdots, NAC-conjugated STAT-3 inhibitor (NAC-Drug) and chitosan polymer. The aqueous phase of ME-II will contain two components, Alexa Fluor® 660 NIR dye conjugated to chitosan polymer (chitosan-dye) and DOTA-Gd (III) conjugated-chitosan polymer (chitosan-DOTA-Gd). The ME-III aqueous phase will contain EDC cross-linker and folate-conjugated PGA (PGA-folate) and PGA polymer. In an exemplary embodiment, an ME composition contains 6.0 mL Triton X-100 (neat), cyclohexane (11.0 mL), n-hexanol (4 mL), and 4.0 mL water (i.e. aqueous phase). It is noted that ME-I, ME-II and ME-III vary with respect to their aqueous phase contents.

The surfactant may be any suitable surfactant known in the art. In particular embodiments, the surfactant comprises a non-ionic surfactant, such as Triton X-100 (e.g., an octylphenol ethylene oxide condensate (P-octyl polyethylene glycol phenyl ether)), available from Union Carbide, USA. Alternatively, the surfactant may be any other suitable surfactant material, such as a fatty acid ester, a polyglycerol compound, a polyoxyethylene surfactant, e.g., asBrij-30, Brij-35, Brij-92, Tween-20, and/or Tween-80.

In one embodiment, the microemulsions may also comprise a co-surfactant. In a particular embodiment, the co-surfactant comprises n-hexanol. N-hexanol is believed to stabilize the interface between oil and water along with the primary surfactant. In another embodiment, the co-surfactant comprises sodium bis(2-ethylhexyl) sulfosuccinate (docusate sodium), also sold commercially as Aerosol® OT (AOT). The oil may be any hydrophobic compound, such as one that is immiscible with water, e.g., aliphatic and aromatic hydrocarbons. Non-limiting examples of suitable oils for use in the present invention, e.g. in the first and second microemulsions, include aliphatic and aromatic hydrocarbons, e.g., hexane, heptane, cyclohexane, toluene and benzene. In a particular embodiment, the oil comprises cyclohexane. The water (aqueous phase) to surfactant molar ratio may be any suitable ratio appropriate for the particular materials and application, such as from about 2:1 to about 70:1, and in a particular embodiment about 22:1.

To form the DCNPs, ME-II was added to ME-1 followed by addition of ME-III to the mixture. In ME-I, Qdots will be covalently conjugated to NAC-Drug and the resulting conjugate will be coated with chitosan polymer (DNCP core). The ME-II aqueous components will further coat Qdots and protect drugs. EDC will cross-link chitosan and PGA polymers, forming a stable polymeric shell (DNCP shell). Due to the confined environment of the water droplets, the resulting DCNP size is expected to be about 30 nm.

The produced DNCPs may offer one or more of the following advantages: (i) imageable by both MRI and NIR modalities; (ii) targetable to tumor cells over-expressing folate receptors; (iii) therapeutic as it carries Stat3 SMI (small molecule inhibitor drugs); (iv) particles are highly hydrophilic and stable in phosphate buffer due to their hybrid nature (chitosan-PGA); (v) biocompatible and stable (cross-linked) DNCP shell structure (biodegradation rate is expected to be quite slow due to cross-linking); (vi) non-heavy metal based DNCP core when non-cadmium based ZnS:Mn/ZnS core is selected; (vii) Improved FRET performance is expected for CdS:Mn/ZnS Qdots over ZnS:Mn/ZnS Qdots (as CdS:Mn/ZnS Qdots is excited efficiently at longer wavelength); (viii) DNCP with CdS:Mn/ZnS core may not exhibit cytotoxicity as the core is well protected by the cross-linked DNCP shell; and (ix) hundreds of SMIs (small molecule inhibitors) will be captured in a single particle and they will remain protected from the adverse extra-cellular environment.

The DNCPs are also porous and hydrophilic particles. When the particles are administered to a subject, and thereafter internalized and exposed to the cytosolic glutathione (GSH) environment, the disulfide bond between the active agent and the Qdot may be cleaved by GSH, resulting in the release of the active agent. The rate of release of the active agent will depend on several factors, including the diffusion rate of glutathione, concentration of intra-cellular glutathione, interaction of drug to polymeric shell, and the like. It is highly feasible to establish a sustained drug release mechanism by controlling the thickness of the DNCP shell and degree of cross-linking.

The Qdot fluorescence in the DNCP will be quenched due to an electron transfer process between the nanoparticles' Qdot core and the Qdot's ligands, e.g., active agents. The restoration of Qdot emission will occur once drugs are released from Qdot surface upon interaction with intra-cellular glutathione. In one embodiment, the Qdot and the Alexa Fluor® 660 are present together in the same nanoparticle and are purposely selected to form a FRET pair where the Qdot will serve as a donor (600 nm emission) and the Alexa Fluor® 660 (663 nm excitation and 690 nm emission maxima) will serve as an acceptor. In absence of glutathione, Qdot emission is in the "OFF" state, but Alexa Fluor® emission is in the "ON" state when excited at 663 nm (therefore, trackable by NIR imaging in vivo). The quantification of drug release, for example, may be based on a FRET scheme with Qdot core as the donor and the Alexa Fluor® NIR dye as the acceptor under Qdot excitation. The ratio of emission intensity of Alexa Fluor® 660 (measured at 690 nm) to Qdot (measured at 600 nm) may be directly correlated to the total amount of drugs present in DNCPs (actual concentration of drugs can be quantified by treating DNCPs with excess amount glutathione and measuring drug fluorescence).

It is appreciated that measure of emission intensities at Alexa Fluor® 660 and Qdot peak emission wavelengths is expected to be appropriate to minimize spectral cross-talk while maximizing signal to background ratio. The ratio of emission intensity of Alexa Fluor® to Qdot will likely increase drastically once drug is released from the DNCPs and FRET occurs from Qdots to Alexa Fluor®. It is noted that only drug molecules are expected to escape from the DNCP and both Qdot and Alexa Fluor® 660 will remain integrated within the particle in the chitosan-based shell. The amount of drug release can be quantified in solution experiments, for example, by constructing a calibration curve of the above intensity ratio versus drug concentration. This calibration curve can be used to estimate drug release in vivo (semi-quantitatively).

As set forth in Table 1 below, several characterization techniques may be utilized to evaluate DNCPs. Without limitation, these techniques include transmission electron microscopy (TEM), scanning electron microscopy (SEM), dynamic light scattering (DLS), UV-visible (UV-VIS) spectroscopy, Fourier transform infrared spectroscopy (FTIR), zeta potential, high pressure liquid chromatography-mass spectrometry (HPLC-MS), NMR/IR, mass spectrometry, fluorescence excitation and emission spectroscopy and fluorescence microscopy, near infrared (NIR) imaging (NIRS), and magnetic resonance (MR) imaging and spectroscopy. Exemplary uses for each technique with respect to the nanoprobes described herein are set forth in Table 1 below.

TABLE 1

| Tests | Purposes |
| --- | --- |
| 1. Fluorescence (excitation and emission) spectroscopy | 1. To perform systematic photophysical characterization of DNCP at different stages of development including characterization of drug loading and release |
| 2. Fluorescence Confocal microscopy | 2. To perform microscopic imaging of DNCP internalized cancer cells to investigate localization of particles and their fate in intracellular environment |
| 3. Electron microscopy (transmission/scanning) | 3. To evaluate DNCP size and morphology |
| 4. Dynamic light scattering | 4. To evaluate DNCP size distribution and to study their state of dispersion in phosphate buffer. |
| 5. Zeta Potential Measurement | 5. To evaluate DNCP surface charge |
| 6. UV-VIS measurement | 6. To characterize absorption of DNCP |
| 7. NMR/IR spectroscopy | 7. To characterize Stat3 inhibitor, Qdot-NAC-Stat 3 conjugate, EDC based covalent coupling (cross-linking) |
| 8. FTIR | 8. To characterize chemical structure using infrared (IR) spectroscopy |
| 9. HPLC-MS | 9. To characterize drug loading |
| 10. Mass Spec | 10. To characterize Stat3 inhibitor construct |
| 11. NIR Imaging | 11. To perform optical based in vivo tumor imaging at NIR region |
| 12. MR imaging and spectroscopy | 12. To determine T1, T2 and T2* for agar phantom embedded with DNCP loaded cancer cells as well as tumor tissue |

The present inventors have undertaken a successful synthestis of DNCP that comprise Qdot-STAT3 small molecule inhibitor (SMI) conjugates and have observed Qdot fluorescence quenching, SMI fluorescence quenching, Qdot and STAT3 restoration upon treatment with glutathione, and folate receptor-mediated specific uptake as with the MMC-NPs set forth above. Further, the present inventors have observed Qdot fluorescence restoration of the DCNPs in MDA-MB-231 cells upon interaction with the intra-cellular glutathione. A few exemplary benefits and uses of the DNCPs are further summarized in Table 2 below.

TABLE 2

| Objectives | Approach |
|---|---|
| i) Specific delivery of anticancer drugs to tumor cells | i) Via folate-receptor mediated targeting |
| ii) Promoting drug stability | ii) By encapsulating drugs within DNCP core |
| iii) Tracking drugs in vivo | iii) By MRI (Gd-DOTA) and NIR (Alexa Fluor 660) imaging of DNCP |
| iv) Confirmation of drug release in vivo | iv) Drug conjugated Qdots are in fluorescently quenched ("OFF") state due to electron/energy transfer process. Drug release process will restore Qdot fluorescence ("ON" state). The "ON" state Qdot will turn on NIR emission of Alexa Fluor through fluorescence resonance energy transfer (FRET) process. |
| v) Quantification of drug concentration within tumor tissue | v) By measuring ratio of fluorescence intensity of Alexa Fluor (at 690 nm) to Qdot (at 600 nm). The ratio will increase with the release of drugs from DNCP. |
| vi) Monitor tumor size | vi) by measuring volume of MRI as well as NIR 3D image contrast volume) |
| vii) Track tumor cells | vii) By MRI and NIR imaging. High T1 relaxivity of DNCP is the key and tracking of a few tumor cells together is feasible. Bright NIR emission from Alexa Fluor will minimize tissue scattering and auto-fluorescence, thus improving optical imaging sensitivity down to a cluster of tumor cells. |
| viii) Monitor tumor metastasis | viii) Again by MRI and NIR imaging. Due to high MRI and optical sensitivity of the DNCP, imaging of metastatic tumor cells is highly feasible. For monitoring tumor metastasis over a period of time, multiple administration of DCNP buffer formulation will be required. |

According to another embodiment, the invention pertains to a nanoprobe comprising an inorganic core or an inorganic/Qdot hybrid core. Either of these core components are associated with an activatable active agent. In one embodiment, the active agent is one that will be released from the core upon exposure to an endogenous molecule, such as glutathione. The nanoprobe is also at least partially or fully encased in a lipid vesicle. In a more specific embodiment, the lipid vesicle is functionalized to promote cellular uptake. Non-limiting examples of functionalization, e.g., surface functionalization, is the linkage of folic acid and/or TAT-peptide to the lipid vesicle.

A non-limiting list of other phospholipids that may be used to form lipid vesicles includes but is not limited to, one or more of hydrogenated soy phosphatidylcholine (HSPC), egg phosphatidylcholine (EPC), phosphatidylethanolamine (PE), phosphatidylglycerol (PG), phosphatidylinsitol (PI), mono-sialogangolioside, spingomyelin (SPM), distearoylphosphatidylcholine (DSPC), dimyristoylphosphatidylcholine (DMPC), or dimyristoylphosphatidylglycerol (DM PG). In certain embodiments of the invention, the ratio of pharmaceutical agent to lipid-protein ranges from about 0.0005 to about 1 (w/w), more preferably about 0.0005 to about 0.5 (w/w), more preferably about 0.001 to about 0.1 (w/w).

Phospholipids preferably form an important part of liposomes. Phospholipids are, in their simplest form, composed of glycerol bonded to two fatty acids and a phosphate group. The resulting compound called phosphatidic acid contains a region (the fatty acid component) that is fat-soluble along with a region (the charged phosphate group) that is water-soluble. Most phospholipids also have an additional chemical group bound to the phosphate. For example, if the phosphate is connected with choline; the resulting phospholipid is called phosphatidylcholine, or lecithin. Other phospholipids include phosphatidylglycerol, phosphatidylinositol, phosphatidylserine, and phosphatidylethanolamine. The fat-soluble portions associate with the fat-soluble portions of other phospholipids while the water-soluble regions remain exposed to the surrounding solvent. The phospholipids of the cell membrane form into a sheet two molecules thick with the fat-soluble portions inside shielded on both sides by the water-soluble portions. This stable structure provides the cell membrane with its integrity.

The components of liposomes determine the physical characteristics of the liposome. Liposomes preferably consist of amphipathic lipid molecules, with phospholipids being the major component. Most commonly, phosphatidylcholine is used as the primary constituent. Other lipids, including phosphatidylethanolamine, phosphatidylserine, sphingomyelin, glycolipids and sterols are often added. The physical characteristics of liposomes depend on pH, ionic strength and phase transition temperatures. The phase transition consists of a closely packed, ordered structure, called as the gel-state, to a loosely packed, less-ordered structure, known as the fluid state. The phase transition temperature ($T_c$) depends on the acyl chain length, degree of saturation, and polar head group. For example, the $T_c$ of egg phosphatidylcholine with a high degree of unsaturation of the acyl chains and varying chain length is −15 degrees C. However, in a fully saturated distearoylphosphatidylcholine (DSPC), $T_c$ is over 50 degrees C. Most liposomal formulations contain cholesterol in order to form a more closely packed bilayer system during preparation. Cholesterol addition to phosphatidylcholine changes the melting behavior of the bilayer, as cholesterol tends to eliminate the phase transition. Cholesterol addition has a condensing effect on the fluid-state bilayer and strongly reduces bilayer permeability.

The fusion of lipid vesicles has been demonstrated to be a powerful approach to create a continuous and fluid lipid membrane on planar solid substrates. (Sackmann, E., Supported Membranes: Scientific and Practical Applications. *Science* 1996, 271, 43.) Recently, there are several reports on the formation of lipid bilayers on nanoparticles by the fusion of small unilamellar vesicles. (e.g., Cauda, V.; Engelke, H.; Sauer, A.; Arcizet, D.; Brauchle, C.; Radler, J.; Bein, T., Colchicine-Loaded Lipid Bilayer-Coated 50 Nm Mesoporous Nanoparticles Efficiently Induce Microtubule Depolymerization Upon Cell Uptake. *Nano Letters* 10, 2484; Li, P. C.; Li, D.; Zhang, L. X.; Li, G. P.; Wang, E. K., Cationic Lipid Bilayer Coated Gold Nanoparticles-Mediated Transfection of Mammalian Cells. *Biomaterials* 2008, 29, 3617; or Mornet, S.; Lambert, O.; Duguet, E.; Brisson, A., The Formation of Supported Lipid Bilayers on Silica Nanoparticles Revealed by Cryoelectron Microscopy. *Nano Letters* 2005, 5, 281) It has been shown that the structure of nanoparticle-supported lipid bilayers is similar to that formed on planar substrates. The coating of lipid bilayers include the enhancement of the circulation time, accumulation of nanoparticles in cells and the minimization of the toxicity of nanoparticles.

In a specific embodiment, the invention pertains to a method of producing a nanoprobe encased in a lipid vesicle.

In a more specific embodiment, CdS:Mn/ZnS Qdots are synthesized in a modular fashion following three steps.

In a first step, unmodified (bare) Qdots are synthesized using a dioctyl sulfosuccinate sodium salt (AOT)/heptane/water microemulsion system as described in the literature. (Santra, S.; Yang, H. S.; Holloway, P. H.; Stanley, J. T.; Mericle, R. A., Synthesis of Water-Dispersible Fluorescent, Radio-Opaque, and Paramagnetic Cds: Mn/Zns Quantum Dots: A Multifunctional Probe for Bioimaging. *Journal of the American Chemical Society* 2005, 127, 1656; Santra, S.; Yang, H.; Dutta, D.; Stanley, J. T.; Holloway, P. H.; Tan, W. H.; Moudgil, B. M.; Mericle, R. A., Tat Conjugated, Fitc Doped Silica Nanoparticles for Bioimaging Applications. *Chemical Communications* 2004, 2810)

In a second step, S3I drug (containing a secondary non-functional amine group) will be chemically linked to NAC using standard EDC (1-ethyl-3-(3-dimethylaminopropyl) carbodiimide, water soluble) coupling chemistry (as described in reference (Santra, S.; Liesenfeld, B.; Dutta, D.; Chatel, D.; Batich, C. D.; Tan, W. H.; Moudgil, B. M.; Mericle, R. A., Folate Conjugated Fluorescent Silica Nanoparticles for Labeling Neoplastic Cells. *Journal of Nanoscience and Nanotechnology* 2005, 5, 899)) to obtain the NAC-S3I conjugate. A 1:1 molar ratio of NAC:S3I may be used to avoid the presence of excess NAC in the reaction mixture. In a previous paper, small lipid vesicles of Zwitterionic 1,2-bis(tricosa-10,12-diynoyl)-sn-glycero-3-phosphocholine (DC8,9PC) were synthesized by dissolving lipid molecules in water at a concentration of 2 mg/mL. The lipid solution was incubated at 50 degrees C. for 3 hours and then extruded 10 times through a Nucleopore membrane using a Lipex extruder. FIG. 19a shows an AFM image of resulting vesicles.

Lastly, the NAC-S3I conjugate is reacted with the unmodified Qdots to obtain S3I surface conjugated Qdots. The product, Qdot-S3I conjugates, may be separated from the microemulsion system by thorough washing with 95% ethanol. These particles are then be further surface modified with a lipid bilayer (LB) to obtain LB coated QDot-S3I. Upon reaction with intracellular GSH, the disulfide bond between the QDot core and NAC-S3I construct is cleaved, thus releasing the drug from the QDot surface and resulting in restoration of quenched Qdot fluorescence in proportion to amount of drug released, as schematically illustrated in FIG. 17.

As described above, the nanoprobes may be coated with lipid bilayers through the fusion of small unilamellar vesicles. In a specific embodiment, Zwitterionic lipid (DC8,9PC), positively charged lipid 1,2-dioleoyl-3-rimethylammonium-propane (DOTAP) (FIG. 19b), and 1-hexadecanoly,2-(9Z,12Z-octadecadienoyl)-sn-glycero-3-phosphatidylethanolamine (PtdEtn) (FIG. 19c) is used. First, small unilamellar vesicles of DC8,9PC, DOTAP and PtdEtn with diameters in the range of 15-50 nm are prepared by extrusion of hydrated lipid films through filters with a pore size at the nanometer scale with standard protocols. (Mayer, L. D.; Hope, M. J.; Cullis, P. R., Vesicles of Variable Sizes Produced by a Rapid Extrusion Procedure. *Biochimica Et Biophysica Acta* 1986, 858, 161). The lipid bilayers obtained from PtdEtn or DOTAP/PtdEtn mixtures can be further modified with folic acid or TAT-peptide by covalently linking to the amine group of PtdEtn. Second, the zeta potential of lipid bilayer-coated Qdots is measured and small unilamellar vesicles to confirm the fusion on Qdots. Third, the formation of lipid bilayers on QDots is observed with cryotransmission electron microscope, which has been used in imaging the lipid bilayers on silica nanoparticles. (Liu, J. W.; Jiang, X. M.; Ashley, C.; Brinker, C. J., Electrostatically Mediated Liposome Fusion and Lipid Exchange with a Nanoparticle-Supported Bilayer for Control of Surface Charge, Drug Containment, and Delivery. *Journal of the American Chemical Society* 2009, 131, 7567). The resulting biosensor particles are shown in FIGS. 18a-b. In particular, FIGS. 18a-b shows a nanoparticle 10 having a CdS:Mn/ZnS quantum dot core 12, to which an S3I inhibitor drug 14 will be covalently linked via a cleavable disulfide bond linkage. (a) a lipid bilayer 16 may be overcoated on the surface of the S3I conjugated CdS:Mn/ZnS quantum dots. (b) the lipid bilayer may be further functionalized with folic acid 18 as shown in FIG. 18b to target cancer cells that overexpress folate receptors, or with TAT peptide (a cellpenetrating peptide).

In an alternative embodiment, the invention pertains to an activatable nanoprobe. The nanoprobe embodiment comprises a core component that is associated with an active agent. The core component may comprise an inorganic core component. Alternatively, the core component may comprise an inorganic/Qdot hybrid core. The active agent may be associated with a linker comprising a double sulfide bond. The construction of the nanoprobe allows for activation of the active agent when exposed to an endogenous compound such as GSH. Thus, certain nanoprobe embodiments do not necessarily incorporate the use of a Qdot or similar optically detectable means or structure.

The nanoprobes, ligands and compounds described herein may be provided in an effective amount, namely an amount effective to achieve the desired result.

The following examples are intended for the purpose of illustration of the present invention. However, the scope of the present invention should be defined as the claims appended hereto, and the following examples should not be construed as in any way limiting the scope of the present invention.

EXAMPLE 1

The following example more particularly describes the production of an exemplary quantum dot (Qdot)-iron oxide (IO) based multimodal/multifunctional nanocomposite probe (MMCNP) that is optically and magnetically imageable, targetable, and capable of reporting on intracellular drug release events.

1.1 Materials

All the chemicals were used as received. Ferric (III) chloride hexahydrate, Ferrous (II) chloride tetrahydrate, ethylenediamine were purchased from Fluka. Lipoic acid and sodium borohydride were purchased from Sigma-Aldrich. Methyl-PEG-12-NHS, and folic acid were purchased from Fisher Scientific, USA. All the other chemicals and solvents were also purchased from Fisher Scientific, USA. Nanopure water (deionized and filtered water) was used for the following example. Fluorescence spectra were recorded in NanoLog Spec Fluorimeter, Perkin Elmer. The FTIR spectra were recorded in a Perkin Elmer Spectrum 100. UV-Vis spectra were recorded in a Cary Win UV spectrometer. The low and high resolution electron microscopic images were taken in TEM JEOL 1011 and FEI Tecnai F30 TEM instruments respectively.

The STAT-3 inhibitor used was an SF-1-046 drug. The non-phosphorylated salicylic acid-based small-molecule, SF-1-046, belongs to the S3I-201.1066 class of STAT3 inhibitors[31,32]. Compounds in this class, including SF-1-046, are structural analogs of the previously reported lead STAT-3 dimerization disruptor, S3I-201[33]. Consistent with the published reports regarding the activities of the lead and the other members of the second generation class of compounds[31-33], GOLD computational modeling[34] indicated SF-1-046 interacts with the STAT3 SH2 domain (data not shown), disrupting STAT3 SH2 domain:pTyr interactions, and thereby inhibits STAT-3 activation. SF-1-046 was prepared via previously published synthetic protocols[31,32].

1.2 Methods (Synthesis and Surface Modification of Iron Oxide Nanoparticle Cores (IONPs) by Dihydrolipoic Acid)

Figure 12:
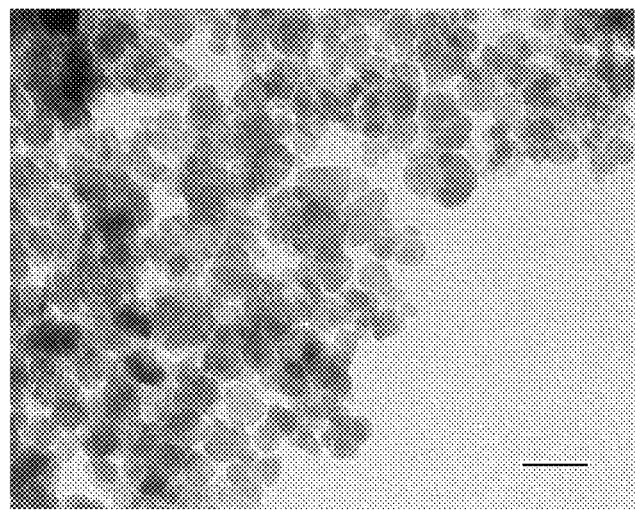
FIG. 12 is a TEM image of a plurality of IONPs showing polydispersity. Bar=20 nm.

Super paramagnetic iron oxide nanoparticles (IONPs) were prepared following a previously established protocol[35]. In brief, 1.0 M (1.13 g) of ferric chloride hexahydrate ($FeCl_3.6H_2O$); 0.5 M (0.415 g) ferrous (II) chloride tetrahydrate ($FeCl_2.4H_2O$); 0.177 mL of 37% HCl in 4 mL of DI water were taken and stirred vigorously in a vortex in 15 mL centrifuge tube. 1.66 mL of 28-30% $NH_4OH$ solution was dissolved in 31 mL of DI water in a conical flask and stirred vigorously for 5 min. Thereafter, the ferric chloride/ferrous chloride/HCl solution was suddenly added to the stirring ammonia solution, and the mixture was stirred again for 30 min with 800 rpm at room temperature in a nitrogen atmosphere to prevent critical oxidation. The black precipitate formed instantly. After complete stirring the iron oxide nanoparticles were separated by sedimentation at the bottom of the flask using an external neodymium magnetic field. 15 mL of the supernatant was decanted and then again the stirring was continued at 800 rpm. 80 mg of lipoic acid (LA) was added in 20 mL chloroform and was vortexed for 20 min. This lipoic acid solution was then added to the iron oxide nanoparticle dispersion shortly. The lipoic acid was used to coat the iron oxide nanoparticles (FIG. 12). After 4 h of complete stirring, 20 mL of methanol was added to reduce the viscosity of the aqueous phase and allowed the chloroform based ferrofluid to settle at the bottom of the container. The clear aqueous phase was first decanted and then the chloroform part was diluted again by 10 mL of chloroform. The chloroform residue was then taken in a separating funnel and washed with water to neutrality. The chloroform part then taken in a 50 mL conical vial and dried under vacuum to get the black solid powder. Thus, lipoic acid-coated iron oxide nanoparticles (LA-IO) were obtained.

To chemically reduce the disulfide bond of LA-IO to dithiol groups, 0.2 g of solid black lipoic acid was coated iron oxide nanoparticles in 50 mL of water/ethanol mixture (1:1), then the dispersion was ultra-sonicated for 10 min, followed by vigorous stirring for another 20 min in ice bath. 0.2 g of ice cold solution of freshly prepared sodium borohydride was slowly added to it under vigorous stirring conditions. After complete addition of the solution, the stirring was continued for another 2 h. The black materials were then separated by sedimentation using a strong neodymium magnet and washed with DI water to neutrality. The material was then taken in choloroform and dried under vacuum to get the solid black dihydrolipoic acid coated iron oxide nanoparticles (DHLA-IO). They were used for the next step of reaction as synthesized.

1.3 Synthesis of CdS:Mn/ZnS Quantum Dots (Qdots).

Dopant based core-shell CdS:Mn/ZnS nanocrystals were used in this example. The CdS:Mn/ZnS Qdots were synthesized by a water-in-oil (W/O) microemulsion method following a published protocol[36]. In brief, cadmium acetate dihydrate ($Cd(CH_3COO)_2.2H_2O$), manganese acetate tetrahydrate ($Mn(CH_3COO)_2.4H_2O$), sodium sulfide ($Na_2S$), and zinc acetate dihydrate, metal basis ($Zn(CH_3COO)_2.2H_2O$) were used for the preparation of $Cd^{2+}$ and $Mn^{2+}$; $S^{2-}$; and $Zn^{2+}$ ion-containing standard aqueous solutions. The aqueous solution was stirred for 15 min and then added to the AOT/heptane solutions to form the water-in-oil (W/O) microemulsions. The Mn-doped CdS core nanocrystals were formed by mixing ($Cd^{2+}$ and $Mn^{2+}$) and $S^{2-}$ containing (W/O) microemulsions rapidly for 10-15 min. The $W_0$ (water-to-surfactant ratio) value of W/O microemulsions were maintained at 10. For the growth of outer shell layer on the Mn doped CdS core Qdots, the $Zn^{2+}$ ion containing (W/O) microemulsion was added at very slow rate (1.5 mL/min) to the (W/O) microemulsions containing CdS:Mn. The nucleation and growth of a separate ZnS phase were suppressed by the very slow addition of the $Zn^{2+}$ containing W/O microemulsion. The $[Zn^{2+}]$ to $[Cd^{2+}]$ molar ratio ($X_0$) was 8 for our study.

1.4 Synthesis of NAC Derivatives of Folic Acid (FA), Drug (STAT3 Inhibitor) and Ethylenediamine (EDA).

Folic acid, drug (STAT3 inhibitor) and ethylenediamine (EDA) were separately conjugated to NAC following standard bioconjugation techniques as described below.

a) STAT3-NAC Conjugation: A 2 mL anhydrous DMSO solution containing $3 \times 10^{-5}$ mol of N-acetyl cysteine, $5.7 \times 10^{-4}$ mol of EDC, and $1.5 \times 10^{-4}$ mol of NHS was stirred for 30 min at room temperature. After this incubation, $1.5 \times 10^{-5}$ mol of solid STAT3 inhibitor compound (contains secondary nonfunctional amine group) was added and whole solution mixture was stirred for 2 h at room temperature. The reaction mixture was passed through 0.2 μm Whatman filter membrane and the solution was then dried under vacuum. The product was dispersed in 1 ml nanopure water (water that has been deionized and then filtered so that no particles greater than 1.0 nanometer remain).

b) EDTA-NAC Conjugatation: Following the same procedure as above for STAT3-NAC, a 2 mL anhydrous DMSO reaction mixture containing $1.2 \times 10^{-4}$ mol of N-acetyl cysteine, $1.2 \times 10^{-3}$ mol of EDC, and $0.3 \times 10^{-3}$ mol of NHS was stirred for 30 min at room temperature. After this incubation, $1.2 \times 10^{-3}$ mol of ethylenediamine (EDTA) was added and the whole reaction mixture was then stirred for another 2 h at room temperature. Then, $N_2$ gas was passed through it followed by filtration through a 0.2 μm Whatman membrane. This solution was then dried under vacuum and the dried product was then dispersed in 1 ml nanopure water.

c) Folic Acid-NAC Conjugation: Following the same procedure as above for STAT3-NAC and EDA-NAC, 2 mL PBS solution containing $2.8 \times 10^{-5}$ mol of folic acid, and $5 \times 10^{-5}$ mol of EDC was stirred for 30 min at room temperature. To this solution, 0.5 ml of the NAC-EDA complex was added. The resulting reaction mixture was then stirred for overnight in dark at room temperature. The reaction mixture was then passed through a 0.2 μm cut-off Millipore® membrane filter. This solution was then dried under vacuum and finally dispersed in nanopure water.

1.5 Synthesis of Qdots Attached to Iron Oxide Nanoparticles (IONPs-Qdots)

In this synthesis process, the CdS:Mn/ZnS core-shell quantum dots (Qdots) were extracted from the microemulsion solution by repeated centrifugation followed by washing several times with methanol and ethanol. The extracted Qdots were dispersible in DI water and used as extracted from microemulsion solution. To the 1 mL Qdots dispersion (20 mg/mL) in water, the DHLA-coated IONP dispersion (2 mg/mL) in 4 mL ethanol was added dropwise. After complete addition, the whole reaction mixture was stirred for overnight. Thereafter, the nanoparticles were separated by a strong external neodymium magnet and washed several times with ethanol and DI water to remove the unused Qdots. In this way, the Qdots were attached on the surface of IONPs through a DHLA linker. The attachment of Qdots on the IONP surface, however, partially reduced the brightness of the Qdot luminescence. The IONP-Qdot composites were bright enough to be easily visualized under illumination by a hand-held 366 nm multiband UV light source. Furthermore, the IONP-Qdot composites responded well to external magnetic fields.

1.6 Surface Functionalization of IONPs-Qdots

The 2 mg/mL IONPs-Qdots nanoparticles were taken in DMSO/ethanol (4:1) mixture and stirred, as well as sonicated to be well dispersed. This dispersion was showing fluorescence under hand-held 366 nm multiband UV light source. This dispersion was then added to a mixture of 0.7 ml of drug (STAT-3)-NAC, 0.2 ml of EDA-NAC and 0.4 ml of FA-NAC conjugates slowly under constant vortexing and UV exposure. It was observed that the previous fluorescence intensity of the IONP-Qdot conjugates was quenched. The reaction was stirred for overnight and then the whole conjugated nanocomposites were separated by a strong external neodymium magnet and washed several times with DMSO and nanopure water. Finally, the reaction mixture was dispersed in 1 ml of 0.1(M) $NaHCO_3$ solution and stirred for few minutes in dark. After this stirring, 5.5 mg of methyl-PEG-NHS ester was added to it and the whole solution was stirred for overnight. These activatable multifunctional/multimodal composite nanoprobes (MMCNPs) were then separated by an external neodymium magnet and washed several times with DPBS (Dulbecco's phosphate buffered saline), and finally was taken in DPBS for further use.

1.7 Preparation of MRI Samples

Human breast cancer (MDA-MB-231), pancreatic cancer (Panc-1), and mouse thymus stromal epithelial (TE-71) cells have all been previously reported[31,32]. Cells were grown in Dulbecco's modified Eagles's medium (DMEM) containing 10% heat-inactivated fetal bovine serum. Cells were treated with the nanoparticles set forth in section 1.6 above at a concentration of 0.1 mg/ml for 24 hours The medium was extracted by vacuum, and cells were washed by 1×PBS buffer for 6 times to remove the unbound nanoparticles. Cells were detached by Trypsin with 0.25% EDTA, centrifuged down at 1500 rpm for 3 minutes and then discarded supernatant. Cells were then resuspended in sterile water and mixed with equal volume 3×PBS and 3% agarose, and carefully poured into 10 mm NMR tubes. Positive control was prepared by mixing 0.3 mg/ml nanoparticles solution with equal volume of 3×PBS and 3% agarose.

1.8 Magnetic Resonance Imaging

Magnetic resonance imaging of a layered cell phantom was performed at 14T magnetic field strength using Paravision 3.0.2 software and a 10 mm microimaging coil (Bruker). A three-dimensional gradient echo scan sequence (FLASH) was acquired with following settings; repetition time (TR)=200 ms, echo time (TE)=2.7 ms, 128×128×128 matrix size and field of view (FOV)=10×10×20 $mm^3$. Hypointense signal from clusters of iron oxide containing cells, was inverted and assigned a red pseudocolor for image presentation on subsequent 3D renderings performed using OsiriX viewing software (http://www.osirix-viewer.com).

1.9 CyQUANT™ Cell Proliferation Assay

Human breast cancer (MDA-MB-231) cells, mouse thymus epithelial stromal (TE-71) cells, and pancreatic cancer (Panc-1) cells were grown in Dulbecco's modified Eagles's medium (DMEM) containing 10% heat-inactivated fetal bovine serum. 5000 cells per well were cultured in 96-well plates. The cells were treated with nanoparticles, compounds (drug), and nanoparticles conjugated to compound for 24 hours. Cyquant cell proliferation assays (Invitrogen Corp/Life Technologies Corp, Carlsbad, Calif.) were then performed on each microplate well. The medium was removed by vacuum, and 50 µL 1× dye binding solution were added to each microplate well, which were then incubated at 37° C. for 30 minutes. The fluorescence intensity of each sample was measured using a fluorescence microplate reader (POLARstar Omega, BMG Labtech, Durham, N.C., USA) with excitation at about 485 nm and emission detection at about 530 nm.

1.10 Confocal Fluorescence Microscopy

The cells were fixed on the glass slide after 24 hrs of incubation with the nanoparticles, compounds (drug), and nanoparticles conjugated to compound. Confocal fluorescence miscroscopy on the cells was done with a home-built sample-scanning confocal microscope. The excitation source was 375 nm pulse diode laser (PicoQuant GmbH, LDH-P-C-375). The power used was 3nW. The laser was focused on a spot size of ~300 nm with a Zeiss 100× Fluar objective lens (NA 1.3, WD 0.17 mm). The sample was raster scanned using a piezoelectric stage (Mad City Labs, Nano-LP100) to get the fluorescence images of the cells with the quantum dots. The fluorescence was detected using the avalanche photodiode (PerkinElmer SPCM-AQR-14). The spectra were collected using a spectrograph with a grating (150 g/mm, blaze: 500 nm) centered at 600 nm (PI Acton SP-2156), which was coupled to a thermoelectrically cooled Electron Multiplying Charge Coupled Device (EM-CCD Andor iXon EM+ DU-897 BI). Spectra were collected from different spots on the cells. Each spectrum was collected with 10 sec exposure time and with three consecutive exposures. These spectra were then averaged in a home-written Matlab program (Mathwork Inc. Natick, Mass.). After taking 100 averaged spectra, they spectra were compiled and an ensemble spectrum was built in Matlab program. The corresponding bright field images were taken by using the same spectrograph with grating (1200 g/mm, blaze: mirror) centered at 4 nm and coupled with EM-CCD. The exposure time for bright field image was 0.05 sec.

1.11 UV-Vis and Fluorescence Measurements

The UV-Vis absorption spectra were collected by using 1 cm path length quartz cuvette with an Agilent 8453 spectrometer. The fluorescence emission spectra were taken by using the 1 cm path length quartz cuvettes with a Nanolog™ Horiba Jobin Yvon fluorometer. The excitation and emission slits were 5 nm. The excitation wavelength was 375 nm for quantum dots and 300 nm for the drug (STAT3 inhibitor (SF-1-046, drug).

In 2 mL of PBS, 100 µL quantum dots in PBS were added and the absorption and emission was taken. Thereafter, 50 µL of 0.3 M solution of GSH was added and absorption and emission spectra were collected immediately after addition of GSH and after every 5 min up to 60 min. This gave a plot of $\lambda_{max}$ emission vs. time in min. After 35 min, the fluorescence was nearly constant showing that the drug is completely released after 35 min.

EXAMPLE 2

In this example, two different water-soluble biomolecules, the N-acetyl cysteine (NAC) and the glutathione (GSH), were used as surface coating ligands for the Qdot nanoparticles. This includes a single-step, one-part synthesis where the Qdot nanocrystals were grown in the presence of the biomolecules. These Qdots were characterized by fluorescence spectroscopy. Stability of the GSH-coated Qdots and the NAC-coated Qdots were studied by treating the coated Qdots with ethylenediaminetetraacetic acid (EDTA, a strong chelating agent for Zn and Cd ions). The results show that fluorescence properties of Qdots are affected by the type of surface coated ligands. In comparison to the GSH-coated Qdots, the NAC-coated Qdots show broad, but strong emission towards near infra-red region. When treated with EDTA, the fluorescence property of the GSH-coated Qdot was affected less than the NAC-coated Qdots. This preliminary study shows that NAC-coated Qdots could thus potentially be used to develop activatable ("OFF/ON") probes for potential deep-tissue imaging applications, the GSH-coated Qdots could thus be applied for probing desired analytes or for bioimaging purposes in environmentally harsh conditions.

2.1 Preparation of GSH-Coated Qdots

A water-in-oil (W/O) microemulsion technique was used to synthesize GSH-coated CdS:Mn/ZnS Qdots at room temperature. The W/O microemulsion system consisted of dioctyl sodium sulfosuccinate (called Aerosol OT or AOT—a surfactant), heptane (oil) and water (as an aqueous phase). Acetate salts of bivalent cadmium, zinc and manganese were using as an ionic source. In a typical procedure, three separate aqueous stock solutions containing acetate salts were prepared using DI water first; Solution A—10.0 mL aqueous solution containing cadmium acetate dihydrate (258.5 mg), 7.4 mg manganese acetate tetrahydrate and 15 mg of GSH; Solution B—5.0 mL aqueous solution containing 257.5 mg sodium sulfide and Solution C—5 mL aqueous solution containing 285.3 mg zinc acetate dihydrate. Next, 35 mL of AOT stock solution was prepared by dissolving 4.46 g of AOT in heptane under magnetic stirring for about 30 mins. Then, solution A1 was prepared by mixing 0.18 mL of stock Solution A with 5 mL of AOT/heptane solution, Solution B1 was prepared by mixing 0.54 mL of stock Solution B with 15 mL of AOT/heptane solution and Solution C1 was prepared by mixing 0.54 mL of stock Solution C with 15 mL of AOT/heptane solution.

Solutions A1, B1 and C1 were then magnetically stirred for 1 hour. Solution A1 was then added to Solution B1 and the resulting mixed solution (Solution AB1) was stirred magnetically for 15 mins. Solution AB1 was added dropwise (using a burette) at a rate 2-3 mL per min to the Solution C1 under magnetic stirring. To obtain maximum brightness from Qdots, this solution mixture should be stirred for 7 days at the room temperature. The GSH-coated CdS:Mn/ZnS Qdots were then isolated from the W/O microemulsion system after precipitating them first using 95% ethanol, followed by repeated washings (6-7 times) with ethanol and ethanol-water mixture to remove surfactants, any un-reacted ions and excess GSH. Ultra-centrifugation technique was used between two successive washing steps to isolate GSH-Qdots in the pellet form from the solution. The NAC-coated Qdots were similarly prepared by adding 15 mg of NAC in Solution A (in place of 15 mg GSH). All the chemicals, reagents and solvents were purchased from Aldrich-Sigma and used without any further purification. The Barnstead Nanopure DI water was used to prepare all the aqueous solutions. Both GSH-Qdots and NAC-Qdots were dispersed well in DI water.

2.2. Fluorescence Study

Both GSH-Qdot and NAC-Qdot exhibited bright yellow emission when exposed to a hand-held UV illumination.

2.3. Excitation of GSH-Qdots

Figure 20:
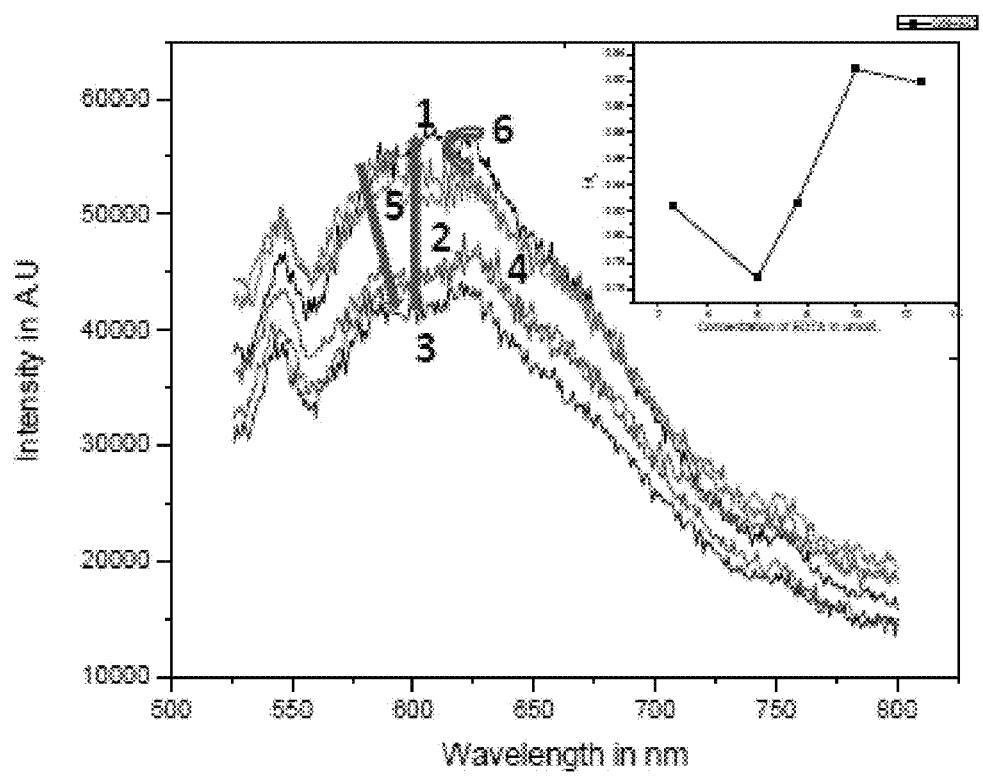
FIG. 20 shows the effect of an increase of EDTA concentration on the fluorescence intensity of GSH-Qdot.
Figure 21:
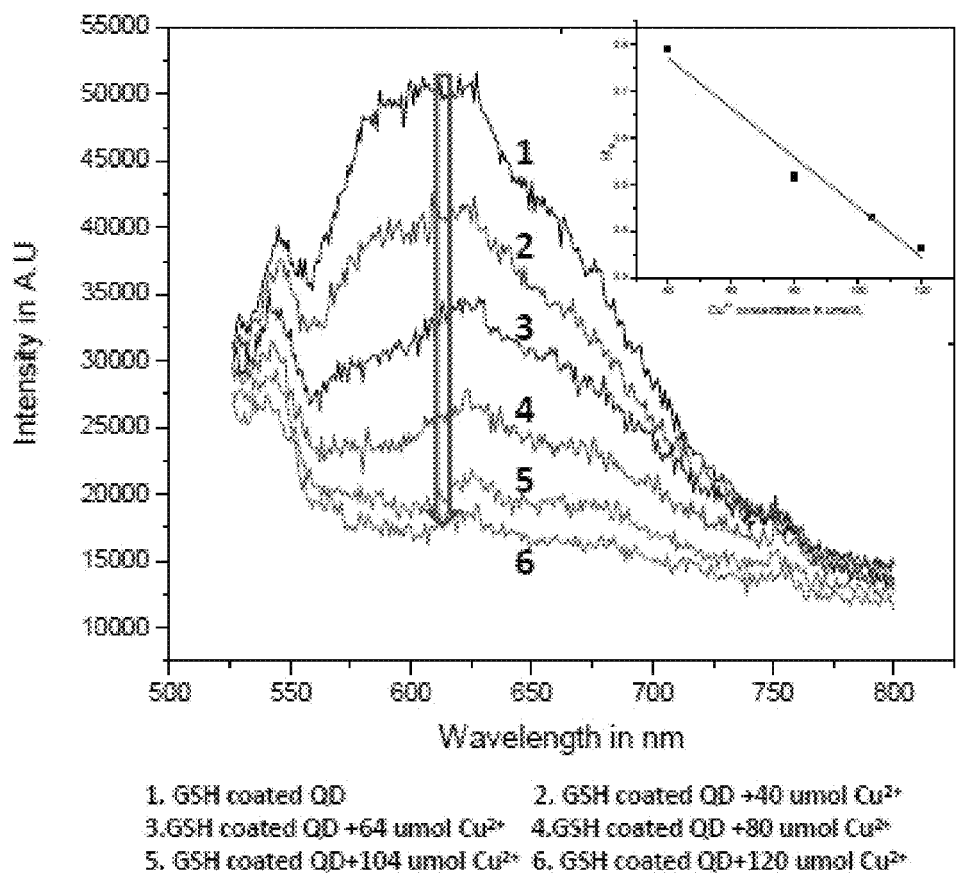
FIG. 21 shows the effect of an increase of Cu ion concentration on the fluorescence intensity of GSH-Qdot.

The GSH coated Qdots emits at ~620 nm upon excitation at 375 nm. In comparison to the NAC-Qdot, the GSH-Qdots are moderately bright. FIG. 20 shows the effect of increase of EDTA concentration on the fluorescence intensity of GSH-Qdot in DI water at the room temperature. No significant change in the fluorescence intensity was observed. Initially, there was a slight quenching (i.e. decrease in the fluorescence intensity) followed by restoration of fluorescence intensity to its initial value. This data suggest that EDTA has minimal effect on the stability of GSH-Qdots, even though EDTA is known to form stable water soluble complex with both the zinc and cadmium ions. The GSH-Qdot fluorescence is however quenched by the copper ions. FIG. 21 shows the effect of increase of Cu ion concentration on the fluorescence intensity of GSH-Qdots. A steady decrease in the fluorescence intensity was observed with the increase in the Cu ion concentration. The inset of the FIG. 21 shows the linear relationship between the fluorescence intensity and the Cu ion concentration. While not wishing to be bound by theory, our results suggest that Cu ions are possibly reacting with the Qdots, forming copper sulfide on the Qdot surface. Due to this chemical transformation the microenvironment of Mn is altered, resulting in the creation of surface related defects. Such defects could result in the increase of non-radiative processes and fluorescence quenching.

2.4 Preparation of NAC-Qdots

Figure 22:
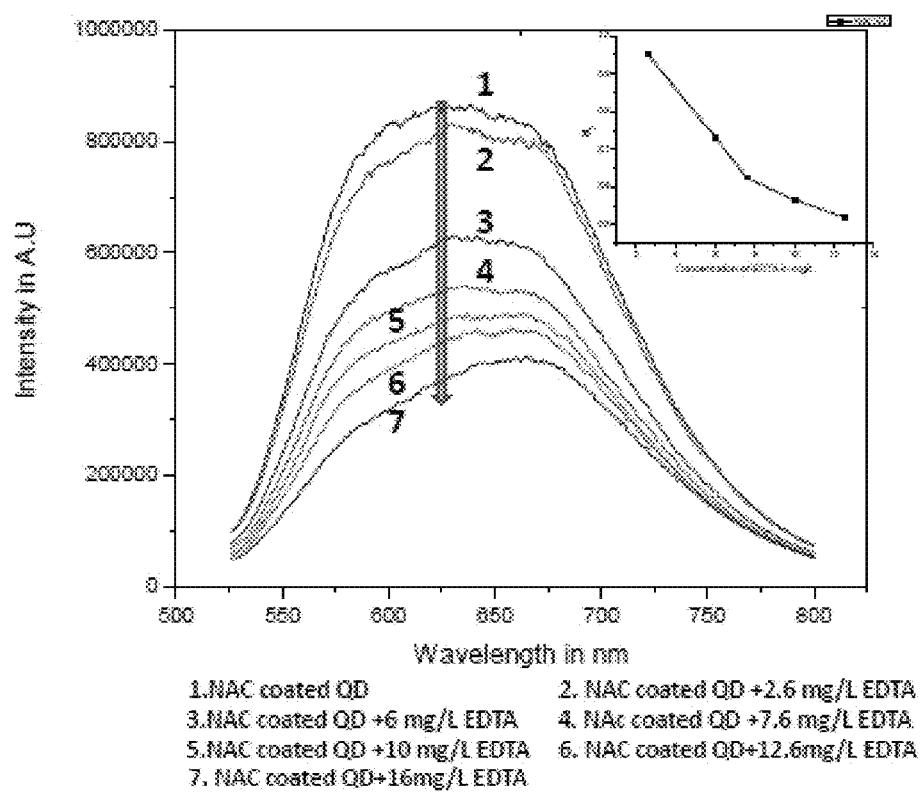
FIG. 22 shows the effect of an increase of EDTA concentration on the fluorescence intensity of a NAC-Qdot.
Figure 23:
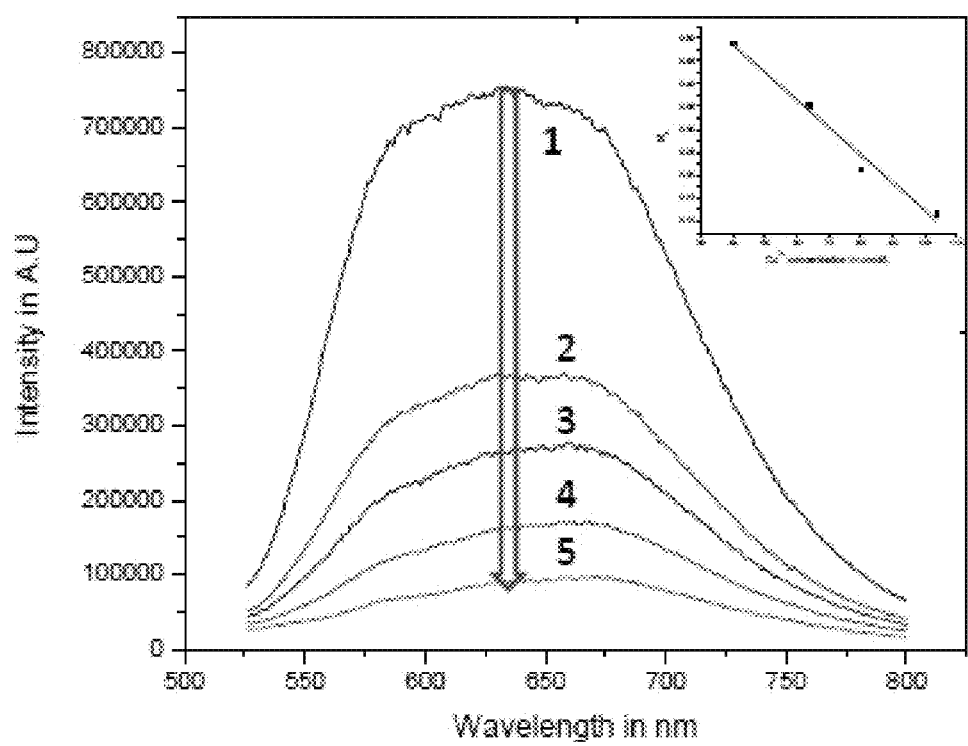
FIG. 23 shows the effect of an increase of Cu ion concentration on the fluorescence intensity of a NAC-Qdot.

The NAC-coated Qdots are highly soluble in DI water and they exhibit extremely bright fluorescence properties. A very broad fluorescence emission in the range 525 nm -800 nm was observed. This broad emission could have been originated due to NAC-induced surface-related defects. FIG. 22 shows the effect of increase of EDTA concentration on the fluorescence intensity of NAC-Qdots. A steady decrease in the fluorescence intensity was observed upon increase in the concentration of EDTA. This observation suggests that NAC-Qdot is not stable against the EDTA chelator. The fluorescence quenching could be due to direct binding of EDTA to the ZnS surface and/or replacement of the NAC by the EDTA. It is well known that EDTA forms a stable complex with Zn ions. A similar observation (i.e. steady decrease in the fluorescence intensity) was made when the NAC-Qdot was exposed to the increasing concentration of Cu ions (FIG. 23). This may be attributed to the formation of Cu sulfide on to the Qdot surface.

In summary, we have described a simple but robust method of making water-soluble CdS:Mn/ZnS at the room temperature. Both the GSH and the NAC are capable of coating Qdot surface via conjugation through their sulfhydryl (—SH) groups and thus forming hydrophilic Qdots. The GSH Qdots are more stable than NAC-Qdots when challenged against a strong chelator, EDTA. The Cu ions are able to quench fluorescence of both the GSH-Qdot and the NAC-Qdot, suggesting the formation of copper sulfide on to the Qdot surface. The NAC-Qdot emission band is broader than the GSH Qdots. Therefore, NAC-Qdots may be used for NIR imaging of biological tissues using two-photon excitation. Our study suggests that NAC-Qdots could be an attractive choice for the fabrication of activatable ("OFF/ON") Qdots for bioimaging and sensing applications.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

REFERENCES, THE ENTIRETY OF EACH OF WHICH IS INCORPORATED BY REFERENCE HEREIN

1. Ferrari, M. Cancer nanotechnology: Opportunities and challenges. *Nature Reviews Cancer* 5, 161-171 (2005).
2. Peer, D., et al. Nanocarriers as an emerging platform for cancer therapy. *Nature Nanotechnology* 2, 751-760 (2007).
3. Foy, S. P., et al. Optical Imaging and Magnetic Field Targeting of Magnetic Nanoparticles in Tumors. *ACS Nano* 4, 5217-5224 (2010).

4. John, R., et al. In vivo magnetomotive optical molecular imaging using targeted magnetic nanoprobes. *Proceedings of the National Academy of Sciences of the United States of America* 107, 8085-8090 (2010).
5. Lee, J. H., et al. All-in-One Target-Cell-Specific Magnetic Nanoparticles for Simultaneous Molecular Imaging and siRNA Delivery. *Angewandte Chemie-International Edition* 48, 4174-4179 (2009).
6. Mulder, W. J. M., et al. Nanoparticulate Assemblies of Amphiphiles and Diagnostically Active Materials for Multimodality Imaging. *Accounts of Chemical Research* 42, 904-914 (2009).
7. Park, K., et al. New Generation of Multifunctional Nanoparticles for Cancer Imaging and Therapy. *Advanced Functional Materials* 19, 1553-1566 (2009).
8. Kircher, M. F., Mahmood, U., King, R. S., Weissleder, R. & Josephson, L. A multimodal nanoparticle for preoperative magnetic resonance imaging and intraoperative optical brain tumor delineation. *Cancer Research* 63, 8122-8125 (2003).
9. McCann, C. M., et al. Combined magnetic resonance and fluorescence imaging of the living mouse brain reveals glioma response to chemotherapy. *Neuroimage* 45, 360-369 (2009).
10. Erogbogbo, F., et al. Biocompatible Magnetofluorescent Probes: Luminescent Silicon Quantum Dots Coupled with Superparamagnetic Iron(III) Oxide. *ACS Nano* 4, 5131-5138 (2010).
11. Mulder, W. J. M., et al. Molecular imaging of tumor angiogenesis using alpha v beta 3-integrin targeted multimodal quantum dots. *Angiogenesis* 12, 17-24 (2009).
12. Mulder, W. J. M., Strijkers, G. J., Nicolay, K. & Griffioen, A. W. Quantum dots for multimodal molecular imaging of angiogenesis. *Angiogenesis* 13, 131-134 (2010).
13. Trehin, R., et al. Fluorescent nanoparticle uptake for brain tumor visualization. *Neoplasia* 8, 302-311 (2006).
14. Zrazhevskiy, P., Sena, M. & Gao, X. H. Designing multifunctional quantum dots for bioimaging, detection, and drug delivery. *Chemical Society Reviews* 39, 4326-4354 (2010).
15. Cheng, S. H., et al. Tri-functionalization of mesoporous silica nanoparticles for comprehensive cancer theranostics-the trio of imaging, targeting and therapy. *Journal of Materials Chemistry* 20, 6149-6157 (2010).
16. Medintz, I. L., et al. Quantum-dot/dopamine bioconjugates function as redox coupled assemblies for in vitro and intracellular pH sensing. *Nature Materials* 9, 676-684 (2010).
17. Medintz, I. L., et al. Proteolytic activity monitored by fluorescence resonance energy transfer through quantum-dot-peptide conjugates. *Nature Materials* 5, 581-589 (2006).
18. Medintz, I. L., Uyeda, H. T., Goldman, E. R. & Mattoussi, H. Quantum dot bioconjugates for imaging, labelling and sensing. *Nature Materials* 4, 435-446 (2005).
19. Medintz, I. L., et al. Self-assembled nanoscale biosensors based on quantum dot FRET donors. *Nature Materials* 2, 630-638 (2003).
20. Banerjee, S., Kar, S., Perez, J. M. & Santra, S. Quantum Dot-Based OFF/ON Probe for Detection of Glutathione. *Journal of Physical Chemistry C* 113, 9659-9663 (2009).
21. Banerjee, S., Kara, S. & Santra, S. A simple strategy for quantum dot assisted selective detection of cadmium ions. *Chemical Communications*, 3037-3039 (2008).
22. Bagalkot, V., et al. Quantum dot—Aptamer conjugates for synchronous cancer imaging, therapy, and sensing of drug delivery based on Bi-fluorescence resonance energy transfer. *Nano Letters* 7, 3065-3070 (2007).
23. Bagalkot, V., et al. Quantum dot—Aptamer conjugates for synchronous cancer imaging, therapy, and sensing of drug delivery based on Bi-fluorescence resonance energy transfer. *Nano Letters* 7, 3065-3070 (2007).
24. Gao, J. H., Gu, H. W. & Xu, B. Multifunctional Magnetic Nanoparticles: Design, Synthesis, and Biomedical Applications. *Accounts of Chemical Research* 42, 1097-1107 (2009).
25. Liong, M., et al. Multifunctional inorganic nanoparticles for imaging, targeting, and drug delivery. *Acs Nano* 2, 889-896 (2008).
26. Mulder, W. J. M., et al. Magnetic and fluorescent nanoparticles for multimodality imaging. *Nanomedicine* 2, 307-324 (2007).
27. Tietze, F. Enzymic method for quantitative determination of nanogram amounts of total and oxidized glutathione—applications to mammalian blood and other tissues. *Analytical Biochemistry* 27, 502-& (1969).
28. Coles, B. & Ketterer, B. The role of glutathione and glutathione transferases in chemical carcinogenesis. *Critical Reviews in Biochemistry and Molecular Biology* 25, 47-70 (1990).
29. Pompella, A., Visvikis, A., Paolicchi, A., Tata, V. D. & Casini, A. F. The changing faces of glutathione, a cellular protagonist. *Biochemical Pharmacology* 66, 1499-1503 (2003).
30. Meier, R., et al. Breast Cancers: MR Imaging of Folate-Receptor Expression with the Folate-Specific Nanoparticle P1133. *Radiology* 255, 527-535 (2010).
31. Zhang, X. L., et al. A novel small-molecule disrupts Stat3 SH2 domain-phosphotyrosine interactions and Stat3-dependent tumor processes. *Biochemical Pharmacology* 79, 1398-1409 (2010).
32. Fletcher, S., et al. Disruption of Transcriptionally Active Stat3 Dimers with Non-phosphorylated, Salicylic Acid-Based Small Molecules: Potent in vitro and Tumor Cell Activities. *Chembiochem* 10, 1959-1964 (2009).
33. Siddiquee, K., et al. Selective chemical probe inhibitor of Stat3, identified through structure-based virtual screening, induces antitumor activity. *Proceedings of the National Academy of Sciences of the United States of America* 104, 7391-7396 (2007).
34. Jones, G., Willett, P., Glen, R. C., Leach, A. R. & Taylor, R. Development and validation of a genetic algorithm for flexible docking. *Journal of Molecular Biology* 267, 727-748 (1997).
35. Robineau, M. & Zins, D. Surfactant-coated particles in magnetic fluids. Characterization and study of thermal stability under inert atmosphere. *Annales De Chimie-Science Des Materiaux* 20, 327-333 (1995).
36. Santra, S., Yang, H. S., Holloway, P. H., Stanley, J. T. & Mericle, R. A. Synthesis of water-dispersible fluorescent, radio-opaque, and paramagnetic CdS:Mn/ZnS quantum dots: A multifunctional probe for bioimaging. *Journal of the American Chemical Society* 127, 1656-1657 (2005).
37. Medintz, I. L., Uyeda, H. T., Goldman, E. R. & Mattoussi, H. Quantum dot bioconjugates for imaging, labelling and sensing. *Nat Mater* 4, 435-446 (2005).
38. Michalet, X. et al. Quantum Dots for Live Cells, in Vivo Imaging, and Diagnostics. *Science* 307, 538-544, doi: 10.1126/science.1104274 (2005).
39. Samia, A. C. S., Chen, X. & Burda, C. Semiconductor Quantum Dots for Photodynamic Therapy. *Journal of the American Chemical Society* 125, 15736-15737, doi: 10.1021/ja0386905 (2003).

40. Shi, L., De Paoli, V., Rosenzweig, N. & Rosenzweig, Z. Synthesis and Application of Quantum Dots FRET-Based Protease Sensors. *Journal of the American Chemical Society* 128, 10378-10379, doi:10.1021/ja0635090 (2006).
41. Medintz, I. L. et al. Self-assembled nanoscale biosensors based on quantum dot FRET donors. *Nat Mater* 2, 630-638 (2003).
42. Bagalkot, V. et al. Quantum Dot-Aptamer Conjugates for Synchronous Cancer Imaging, Therapy, and Sensing of Drug Delivery Based on Bi-Fluorescence Resonance Energy Transfer. *Nano Letters* 7, 3065-3070, doi:10.1021/nl071546n (2007).
43. Zhang, C.-y. & Johnson, L. W. Single Quantum-Dot-Based Aptameric Nanosensor for Cocaine. *Analytical Chemistry* 81, 3051-3055, doi:10.1021/ac802737b (2009).
44. Banerjee, S., Kar, S. & Santra, S. A simple strategy for quantum dot assisted selective detection of cadmium ions. *Chemical Communications*, 3037-3039 (2008).
45. Banerjee, S. & Santra, S. Semiconductor CdS:Mn/ZnS quantum dots for sensing applications. Vol. 7674 (SPIE, 2010).
46. Banerjee, S., Kar, S., Perez, J. M. & Santra, S. Quantum Dot-Based OFF/ON Probe for Detection of Glutathione. *The Journal of Physical Chemistry* C 113, 9659-9663, doi:10.1021/jp9019574 (2009).
47. Mitra, R. N. et al. An activatable multimodal/multifunctional nanoprobe for direct imaging of intracellular drug delivery. *Biomaterials* 33, 1500-1508, doi:10.1016/j.biomaterials.2011.10.068 (2012).

The present application further cross-references US Published Patent Application Nos. 20110021745, 20100254911, 20100254911, 20070269382, 20070264719, 20060228554, each of which is incorporated by reference herein

The invention claimed is:

1. An optically activatable nanoprobe comprising:
    an inorganic core;
    a quantum dot linked to the inorganic core; and
    at least one ligand linked to the quantum dot, the at least one ligand effective to reduce luminescence of the quantum dot when linked thereto.

2. The optically activatable nanoprobe of claim 1, wherein the at least one ligand comprises at least one of an active agent, a targeting agent, a hydrophilic dispersing agent, an imaging agent, or combinations thereof.

3. The optically activatable nanoprobe of claim 2, wherein the at least one ligand comprises each of an active agent, a targeting agent, and a hydrophilic dispersing agent.

4. The optically activatable nanoparticle of claim 3, wherein the active agent comprises a STAT-3 inhibitor, the targeting agent comprises folate, and the hydrophilic dispersing agent comprises polyethylene glycol.

5. The optically activatable nanoprobe of claim 1, wherein the at least one ligand comprises a hydrophilic dispersing agent.

6. The optically activatable nanoprobe of claim 5, wherein the quantum dot comprises a coating of the hydrophilic dispersing agent.

7. The optically activatable nanoprobe of claim 1, wherein the hydrophilic dispersing agent comprises at least one of N-acetyl cysteine and glutathione.

8. The optically activatable nanoprobe of claim 1, wherein the at least one ligand is linked to the quantum dot by N-Acetyl-L-Cysteine.

9. The optically activatable nanoprobe of claim 1, wherein the inorganic core comprises iron oxide, and wherein the quantum dot comprises a CdS:Mn/ZnS quantum dot.

10. The optically activatable nanoprobe of claim 1, wherein the quantum dot is linked to the inorganic core by a linking group, and wherein the linking group comprises a hetero-bifunctional cross-linking molecule.

11. The optically activatable nanoprobe of claim 10, wherein the linking group comprises dihydrolipoic acid.

12. The optically activatable nanoprobe of claim 1, wherein the at least one ligand is linked to the quantum dot by a disulfide bond.

13. The optically activatable nanoprobe of claim 1, wherein the nanoprobe has a particle size of from 20-40 nm.

14. An optically activatable nanoprobe for monitoring intracellular drug delivery comprising:
    a core component; and
    at least one ligand linked to the core component, the at least one ligand comprising at least one of an active agent, a targeting agent, an imaging agent, a hydrophilic dispersing agent and combinations thereof, the at least one ligand being effective to reduce luminescence of the of the quantum dot when linked thereto.

15. The optically activatable nanoprobe of claim 14, wherein the core component comprises an iron oxide core and a plurality of quantum dots linked to the inorganic core.

16. The optically activatable nanoprobe of claim 14, wherein the core component comprises a quantum dot.

17. The optically activatable nanoprobe of claim 14, wherein the core component comprises a quantum dot and a chitosan polymer.

18. The optically activatable nanoprobe of claim 17, wherein the chitosan polymer further comprises a hydrophilic dispersing agent.

19. The optically activatable nanoprobe of claim 14, further comprising a lipid vesicle at least partially or fully encasing the core component and the at least one ligand.

20. The optically activatable nanoparticle of claim 14, wherein the at least one ligand comprises an active agent, a targeting agent, and a hydrophilic dispersing agent, wherein the active agent comprises a STAT-3 inhibitor, the targeting agent comprises folate, and the hydrophilic dispersing agent comprises polyethylene glycol or derivatives thereof.

* * * * *